(12) United States Patent
Hu

(10) Patent No.: US 10,889,763 B2
(45) Date of Patent: Jan. 12, 2021

(54) METHODS AND COMPOSITIONS FOR MICROWAVE-ASSISTED NON-OXIDATIVE CATALYTIC DIRECT CONVERSION OF NATURAL GAS

(71) Applicant: West Virginia University, Morgantown, WV (US)

(72) Inventor: Jianli Hu, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 16/355,501

(22) Filed: Mar. 15, 2019

(65) Prior Publication Data
US 2019/0284481 A1 Sep. 19, 2019

Related U.S. Application Data

(60) Provisional application No. 62/644,022, filed on Mar. 16, 2018.

(51) Int. Cl.
*C10G 5/00* (2006.01)
*B01J 29/40* (2006.01)
(Continued)

(52) U.S. Cl.
CPC ............. *C10G 5/00* (2013.01); *B01J 23/28* (2013.01); *B01J 23/881* (2013.01); *B01J 29/405* (2013.01); *B01J 29/44* (2013.01); *B01J 29/48* (2013.01); *B01J 35/1019* (2013.01); *B01J 35/1038* (2013.01); *B01J 37/0201* (2013.01); *B01J 37/0236* (2013.01); *B01J 37/08* (2013.01); *C01B 39/38* (2013.01); *C07C 2/76* (2013.01);
(Continued)

(58) Field of Classification Search
CPC .................................... C07C 2/76; C07C 2/80
USPC ................ 585/407, 417, 418, 419, 420, 943
See application file for complete search history.

(56) References Cited

U.S. PATENT DOCUMENTS 5,081,324 A  1/1992 Michaels et al.
5,205,915 A  4/1993 Ravella et al.

FOREIGN PATENT DOCUMENTS

CN     1266041    * 9/2000
WO  WO 00/50366  * 8/2000

OTHER PUBLICATIONS

Chen et al., Upgrading of stranded gas via non-oxidative conversion processes, Catalysis Today 310, p. 94-97, 20018.
(Continued)

*Primary Examiner* — Thuan D Dang
(74) *Attorney, Agent, or Firm* — Innovators Legal

(57) ABSTRACT

Disclosed are compositions for catalysts comprising a zeolite promoted by metal and or metal oxide. In some aspects, the metal and/or metal oxide comprise a mixture of two or more metal or metal oxides. In various aspects, the zeolite is a pentasil zeolite and/or a ZSM-5 type zeolite. Also disclosed are processes for making the disclosed heterogeneous catalysts comprising preparing a mixture of a zeolite and one or more metal salts, which can include use of incipient wetness impregnation methods. In various aspects, also disclosed are methods for direct, non-oxidative preparation of higher hydrocarbons from natural gas, including selective for high yield production of C6 and higher hydrocarbons. This abstract is intended as a scanning tool for purposes of searching in the particular art and is not intended to be limiting of the present disclosure.

20 Claims, 21 Drawing Sheets

(51) Int. Cl.

| | |
|---|---|
| *B01J 29/48* | (2006.01) |
| *B01J 29/44* | (2006.01) |
| *B01J 37/02* | (2006.01) |
| *C01B 39/38* | (2006.01) |
| *B01J 37/08* | (2006.01) |
| *B01J 23/28* | (2006.01) |
| *B01J 23/881* | (2006.01) |
| *B01J 35/10* | (2006.01) |
| *C07C 2/76* | (2006.01) |

(52) U.S. Cl.
CPC ..... *B01J 2229/186* (2013.01); *C01P 2002/01* (2013.01); *C01P 2002/72* (2013.01); *C01P 2002/85* (2013.01); *C07C 2521/12* (2013.01); *C07C 2529/40* (2013.01); *C07C 2529/44* (2013.01); *C07C 2529/48* (2013.01); *C10G 2300/1025* (2013.01); *C10G 2300/70* (2013.01); *C10G 2300/80* (2013.01); *C10G 2400/30* (2013.01)

(56) References Cited

OTHER PUBLICATIONS

Qi et al., Methane aromatization using Mo-based catalysts prepared by microwave heating, Catalysis Today 98, p. 639-645, 2004.

Zeng et al., Nonoxidative dehydrogenation and aromatization of methane over W/HZSM-5-based catalysts, Catalysis Letters 53, p. 119-124, 1998.

International Search Report issued for application PCT/US19/22586, dated Jun. 6, 2019.

\* cited by examiner

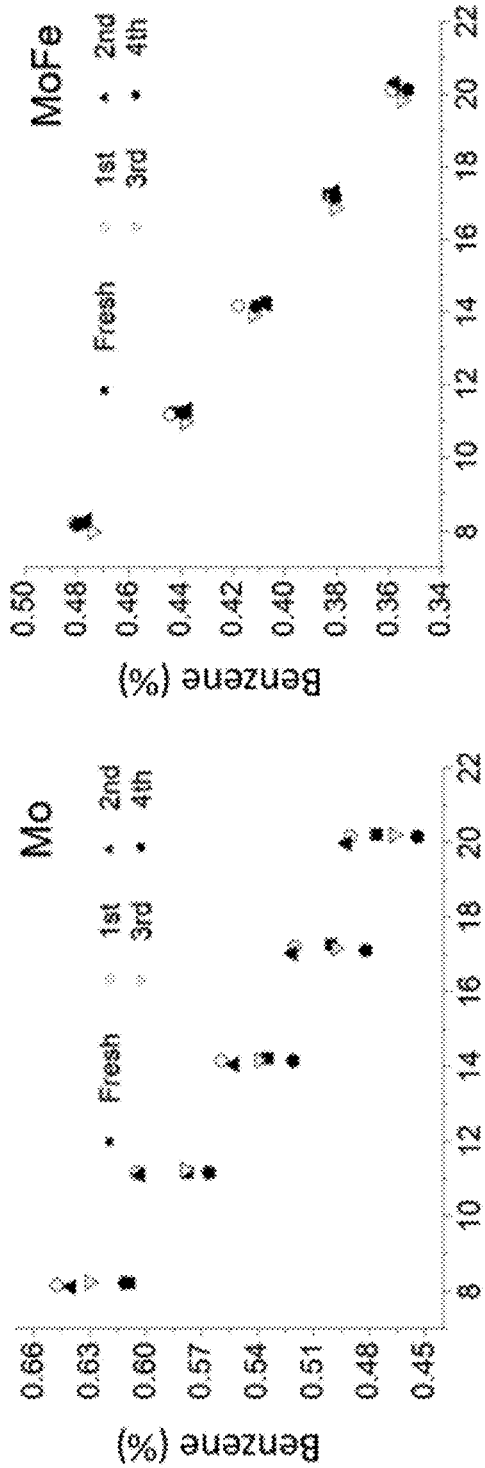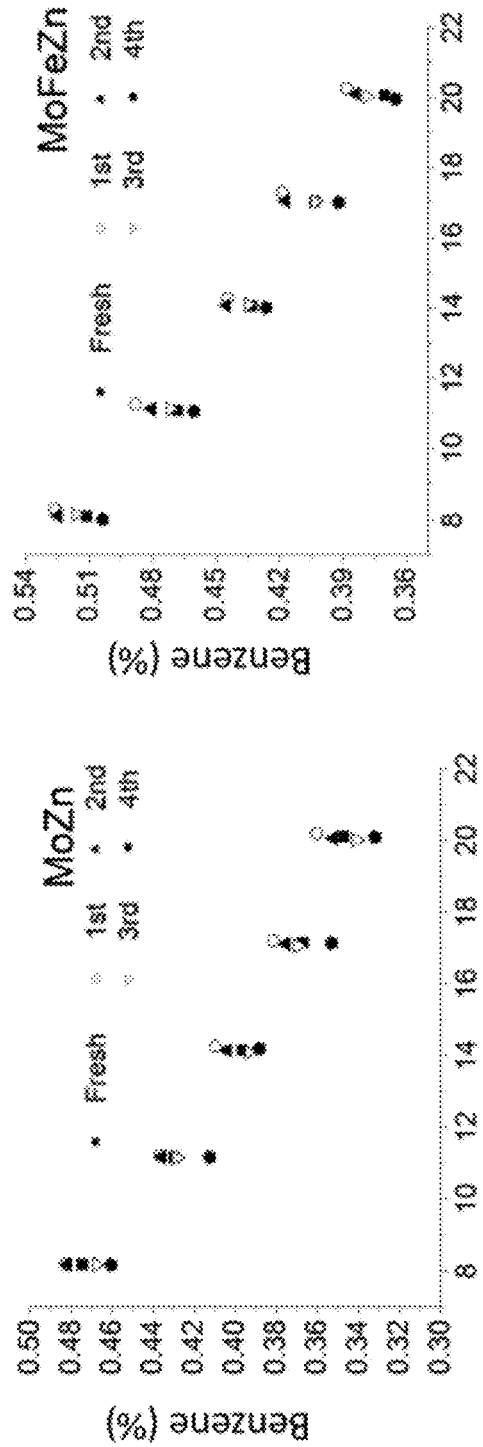

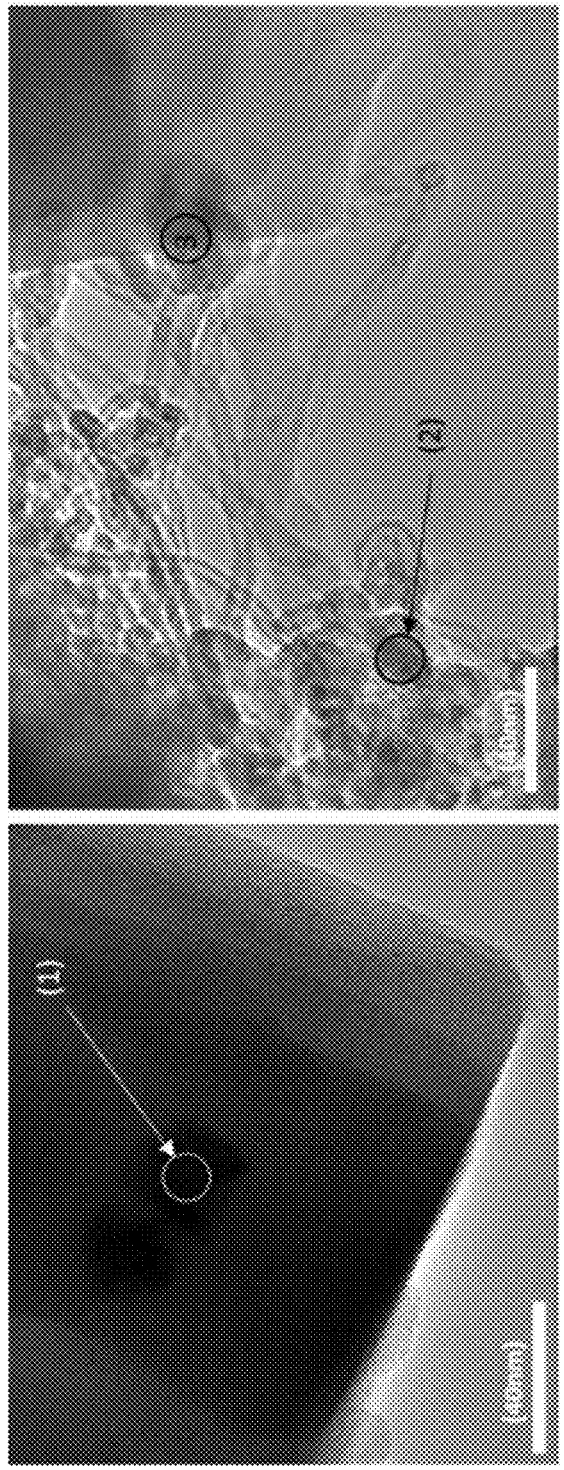

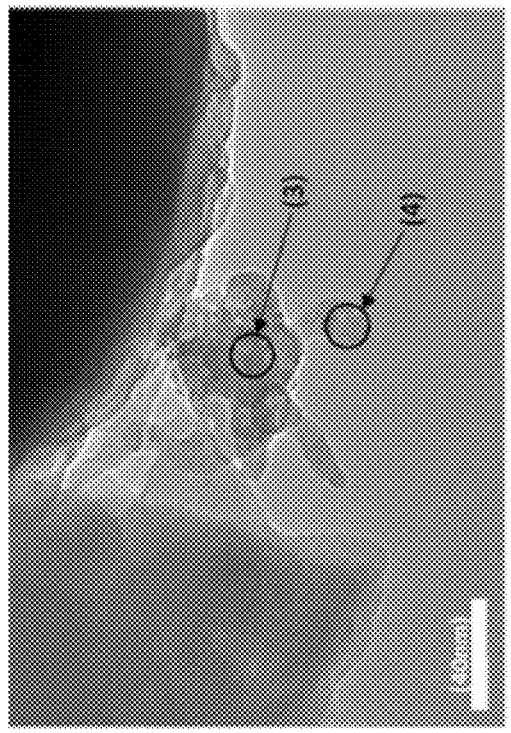
FIG. 14A
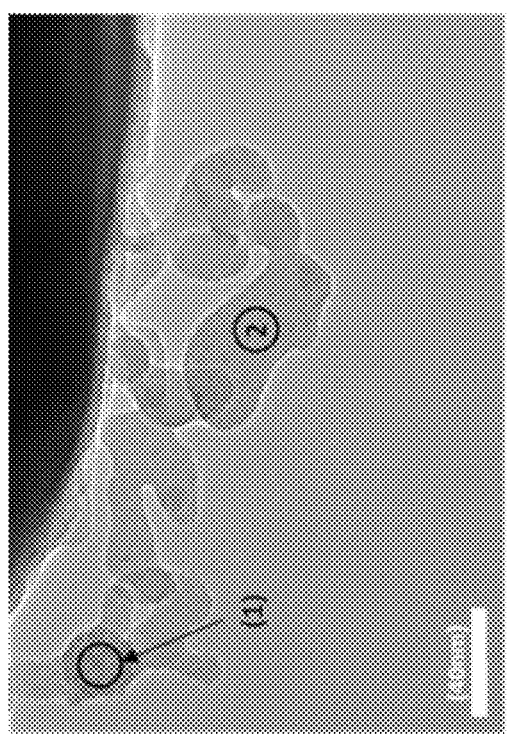
FIG. 14B
| Elements | Atomic % | | | |
|---|---|---|---|---|
| | Spot (1) | Spot (2) | Spot (3) | Spot (4) |
| C | 17.82 | 19.84 | 24.38 | 28.84 |
| O | 63.94 | 67.52 | 54.32 | 44.42 |
| Al | 9.54 | 0.89 | 12.48 | N/P |
| Si | 22.38 | 33.19 | 14.79 | 26.74 |
| Zn | 3.06 | N/P | 2.00 | N/P |
| Mo | 1.72 | N/P | 2.13 | N/P |
FIG. 14C

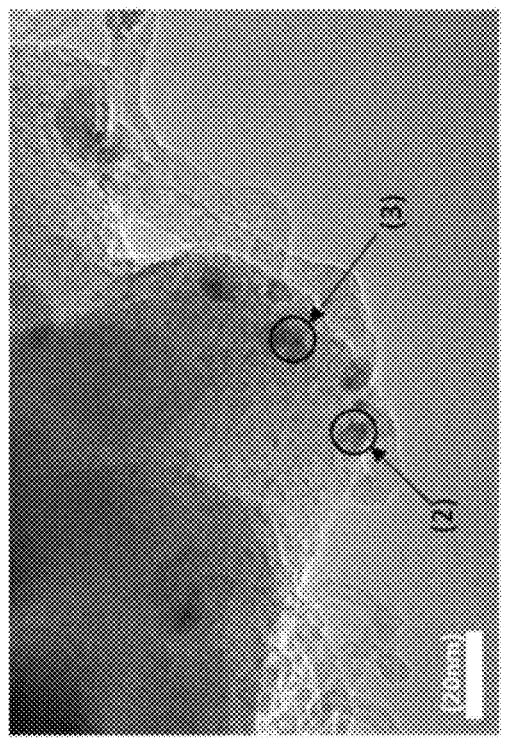
FIG. 15A
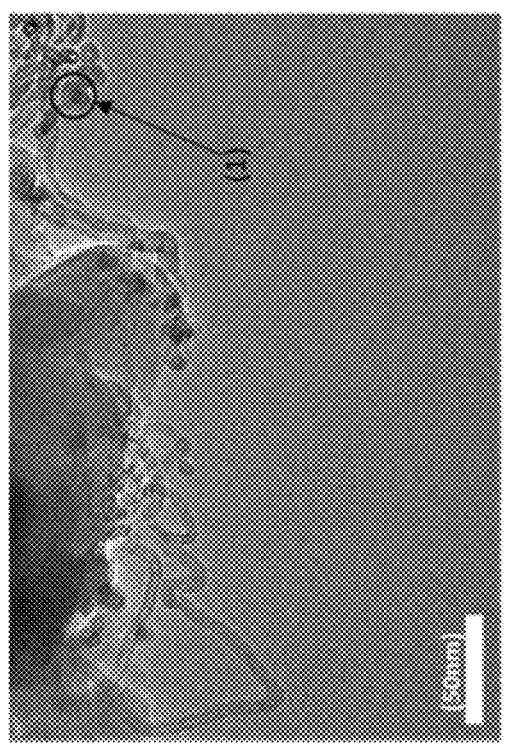
FIG. 15B
| Element | Atomic % | | |
|---|---|---|---|
| | Spot (1) | Spot (2) | Spot (3) |
| C | 93.51 | 65.36 | 59.69 |
| O | N/P | 22.87 | 21.82 |
| Al | N/P | 0.82 | 2.19 |
| Si | N/P | 9.24 | 11.81 |
| Fe | 4.01 | 0.55 | 1.27 |
| Mo | 2.48 | 1.16 | 3.21 |
FIG. 15C

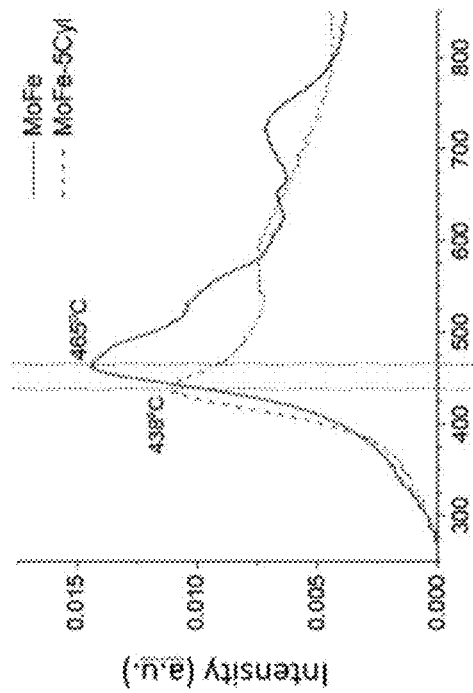
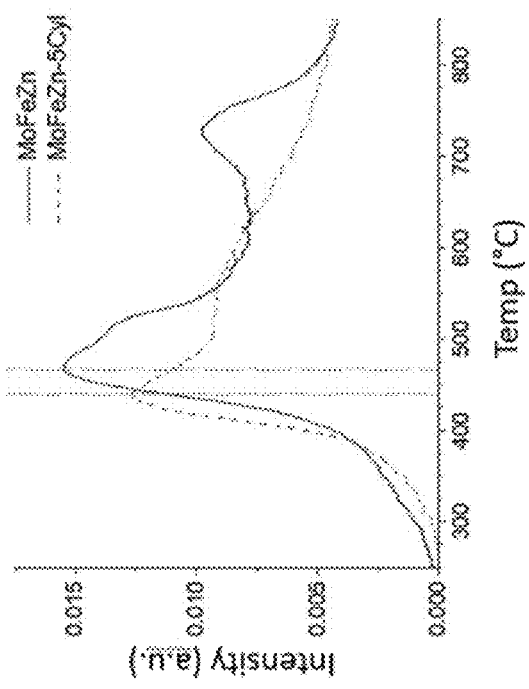
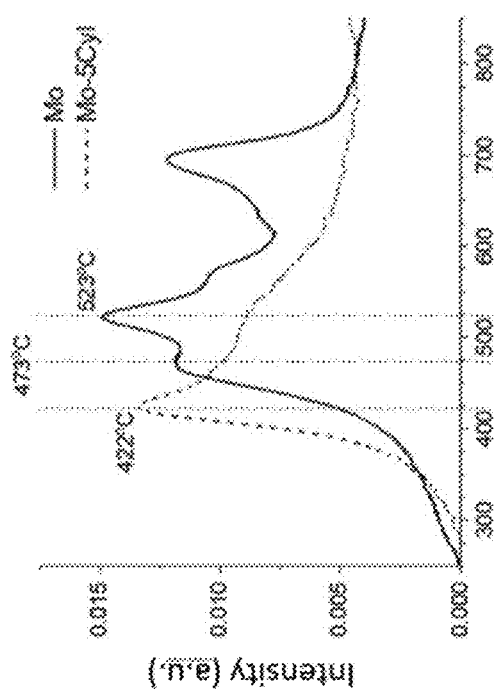
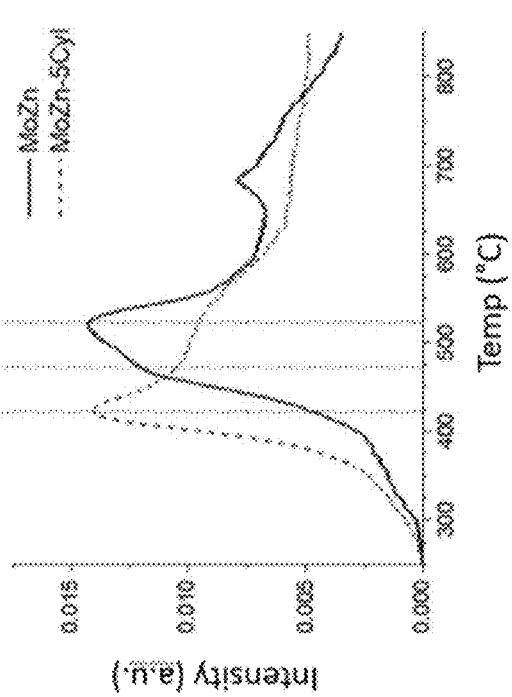
FIG. 16A
FIG. 16B
FIG. 16C
FIG. 16D

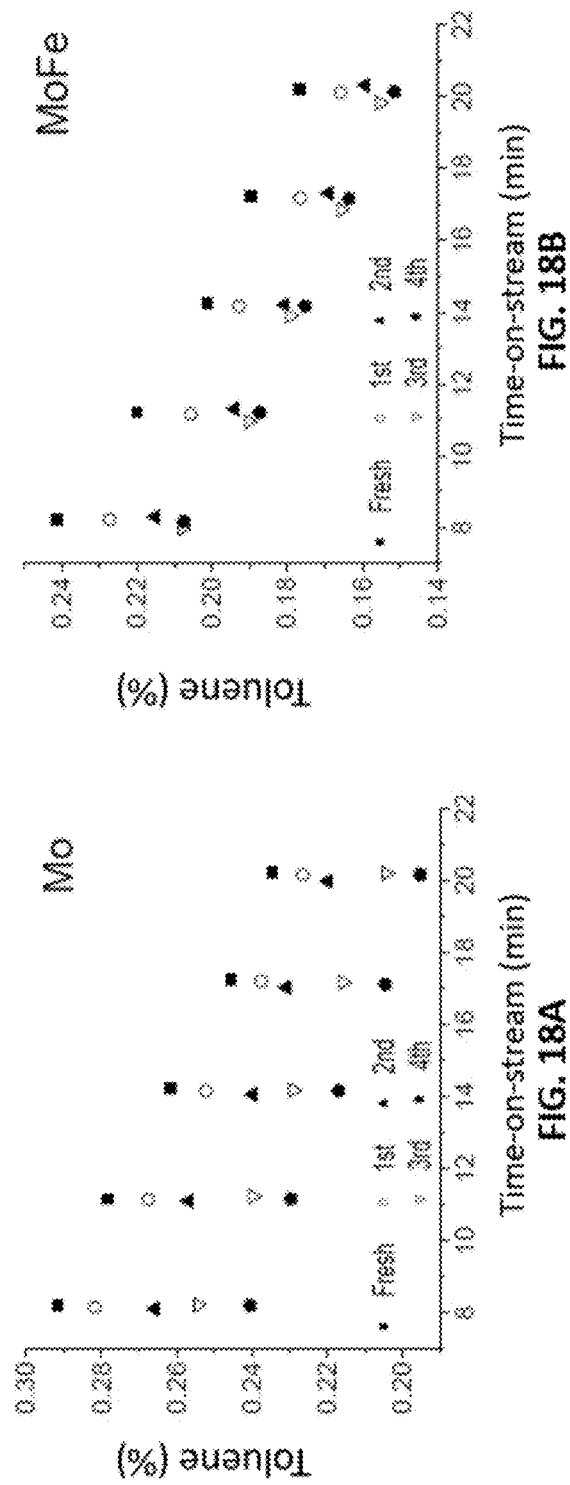
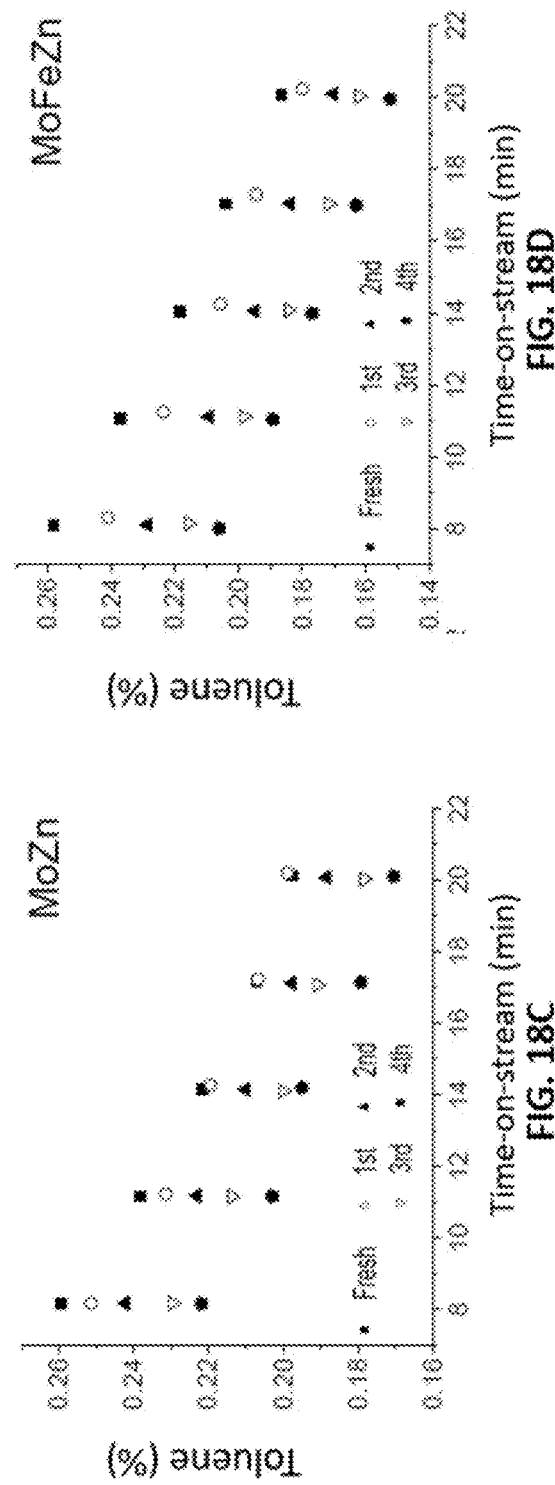
FIG. 18A, FIG. 18B, FIG. 18C, FIG. 18D

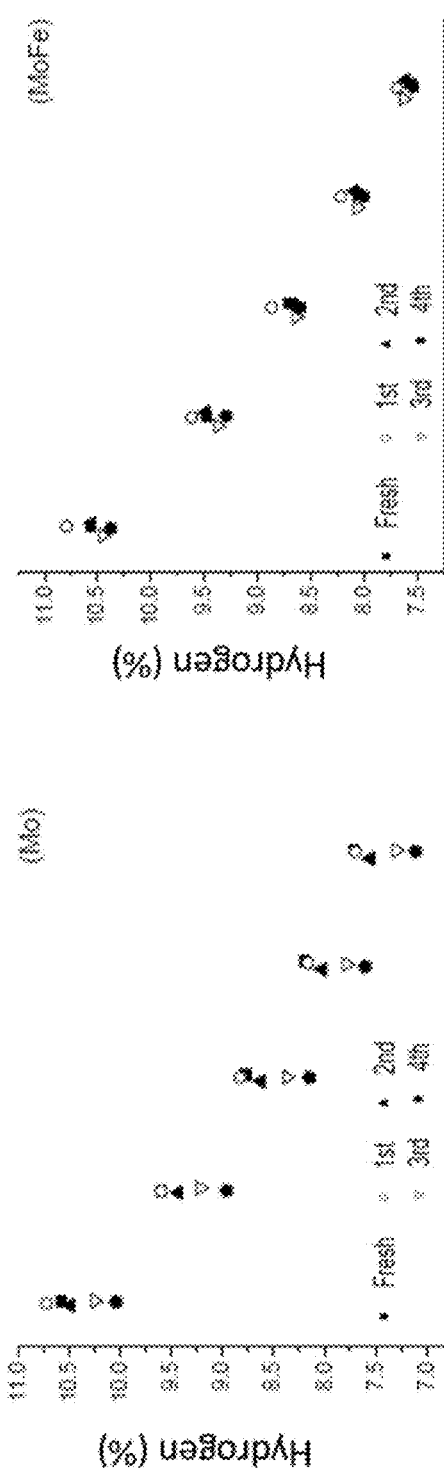
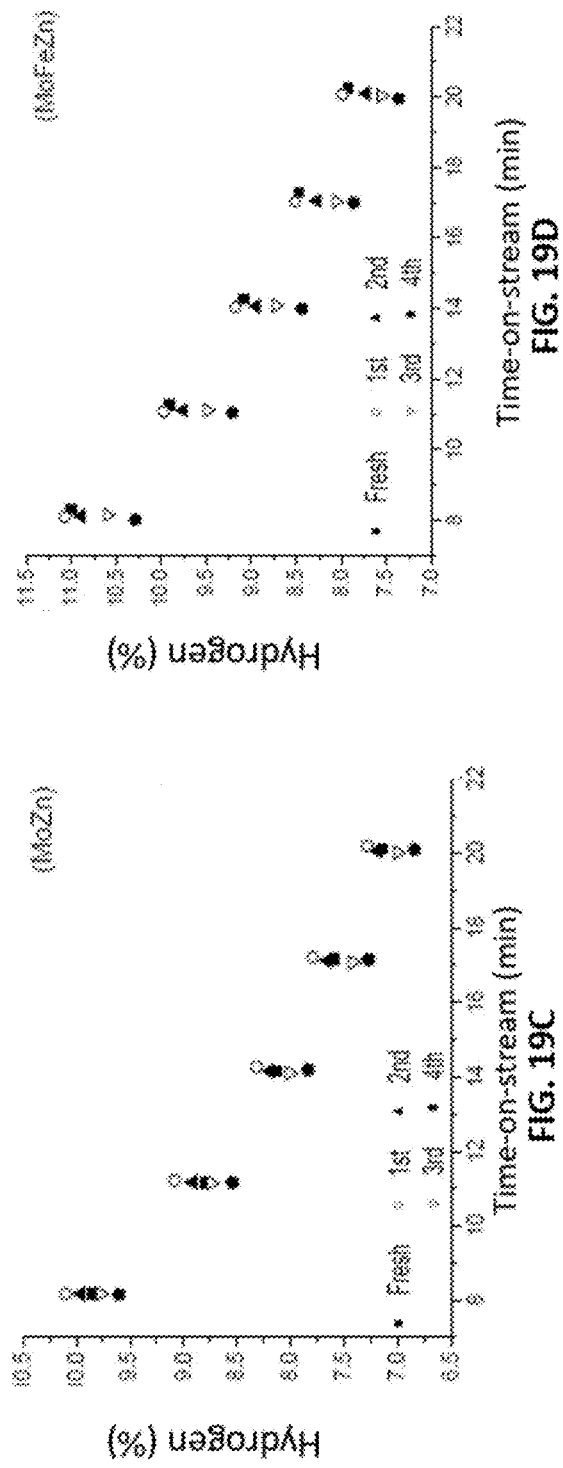
FIG. 19A (Mo)
FIG. 19B (MoFe)
FIG. 19C (MoZn)
FIG. 19D (MoFeZn)

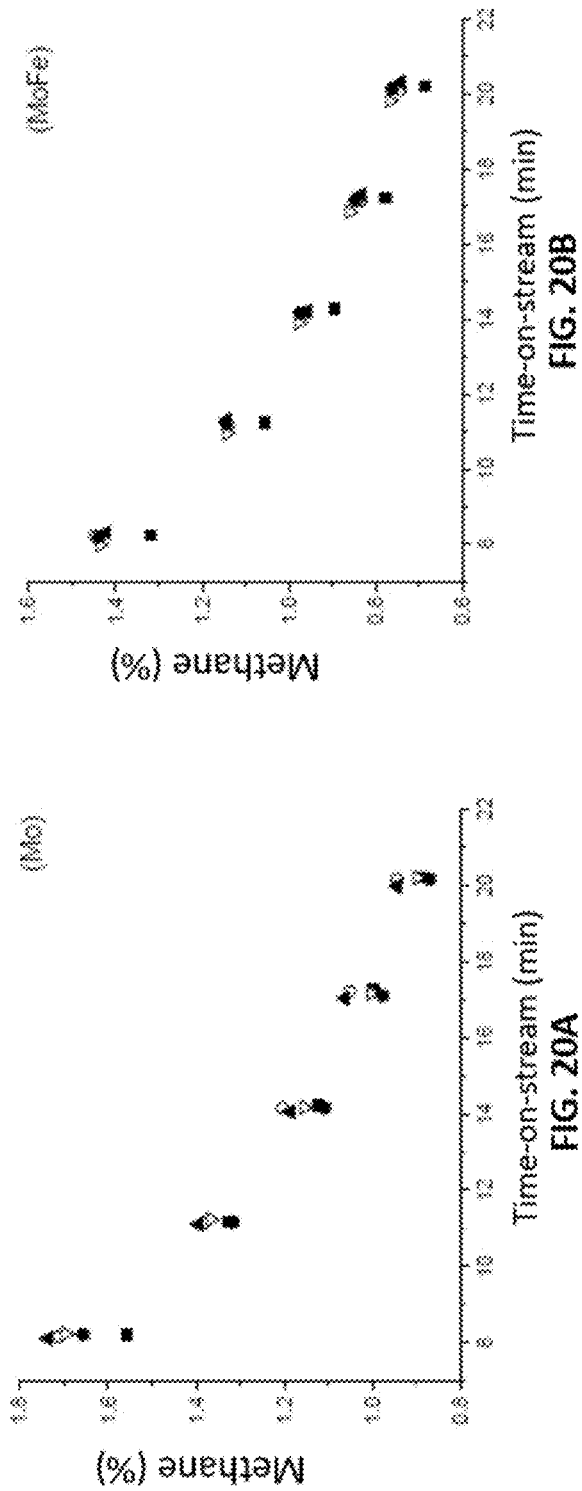
FIG. 20A
FIG. 20B
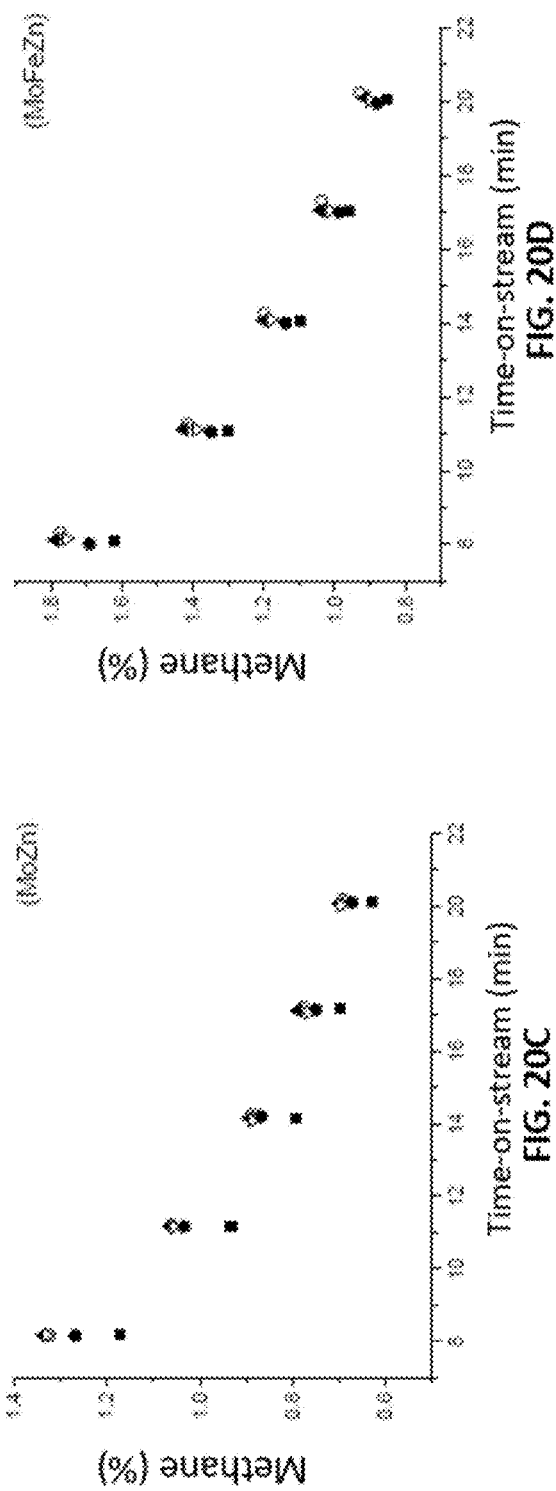
FIG. 20C
FIG. 20D

METHODS AND COMPOSITIONS FOR MICROWAVE-ASSISTED NON-OXIDATIVE CATALYTIC DIRECT CONVERSION OF NATURAL GAS

CROSS-REFERENCE TO RELATED APPLICATIONS

This Application claims the benefit of U.S. Provisional Application No. 62/644,022, filed on Mar. 16, 2018, which is incorporated herein by reference in its entirety.

BACKGROUND

In the chemical industry, aromatics and olefins are mainly produced from petroleum feedstock. However, it is very likely that the long-term price of natural gas will remain much lower than equivalent crude oil; therefore, efficient conversion of natural gas to value-added chemicals presents a significant market need. Conventional commercial natural gas-to-chemical processes are currently based on an indirect route via syngas production. The available indirect routes natural gas-to-chemical processes are generally extremely energy inefficient and capital intensive. In particular, for the currently available natural gas-to-chemical processes, more than 50% of the capital cost is incurred in syngas production, which merely provides an intermediate in the overall process. Furthermore, smaller natural gas sources in remote regions cannot realize the economies of scale exhibited by large gas-to-chemical plants. Moreover, the variation in daily production volume and the change in gas composition, particularly in remote regions, over time are hurdles to the engineering design of large plants.

In contrast, a direct non-oxidative natural gas conversion has the potential to eliminate the syngas production step, with concomitant requirement for oxygen generation. Unfortunately, these technologies have not been commercialized to date because of technical challenges such as low selectivity, coking, heat management in reactor, catalyst deactivation and regeneration. Increased use of natural gas as a feedstock for value-added chemical production will require a commercially and technically feasible solution to direct, non-oxidative conversion of natural gas to chemical feedstacks.

Despite advances in industrial production of value-added chemical feedstocks, the industry continues to rely on petroleum sources despite the availability of significantly less expensive natural gas supplies. In particular, the industry lacks suitably facile processes and compositions for widespread use of natural gas for the production of higher hydrocarbon chemical feedstocks. These needs and other needs are satisfied by the present disclosure.

SUMMARY

In accordance with the purpose(s) of the disclosure, as embodied and broadly described herein, the disclosure, in one aspect, relates to compositions for catalysts comprising a zeolite and a metal oxide. In some aspects, the metal oxide comprises a first metal oxide and a second metal oxide. In further aspects, the metal oxide comprises a mixture of two or more metal oxides. The zeolite used in the catalyst can be any suitable zeolite. In a further aspect, the zeolite is a pentasil zeolite. In a still further aspect, the zeolite is a ZSM-5 type zeolite. The present disclosure further discloses processes for making the disclosed heterogeneous catalysts comprising preparing a mixture of a zeolite and one or more metal salts. In some aspects, the preparation of the catalyst comprises aspects of incipient wetness impregnation. In various aspects, the present disclosure relates to methods for direct, non-oxidative preparation of higher hydrocarbons from natural gas. In a further aspect, the methods for preparation of higher hydrocarbons from natural gas are selective for high yield production of C6 and higher hydrocarbons.

Disclosed are heterogeneous catalysts comprising: a zeolite present in an amount of about 80 wt % to about 99.95 wt % based on the total weight of the catalyst; and a metal oxide present in an amount of about 0.05 wt % to about 20 wt % based on the total weight of the catalyst.

Also disclosed are processes for synthezing a disclosed heterogeneous catalyst, the process comprising: forming a mixture comprising a zeolite and a metal salt solution, wherein the metal salt solution is present as an aqueous solution of a metal salt; wherein the zeolite is present in an amount of about 80 wt % to about 99.95 wt % based on the total weight of the zeolite powder and the metal salt; and wherein the metal salt is present in amount corresponding to about 0.05 wt % to about 20 wt % based on the total weight of the zeolite powder and the metal salt; heating the mixture of the zeolite and the metal salt solution, thereby forming a dried mixture comprising the zeolite and the metal salt; and calcining the dried mixture of the zeolite and metal salt.

Also disclosed are processes for conversion of natural gas to higher hydrocarbons, the process comprising arranging a disclosed heterogenous catalyst in a reaction chamber of a fixed-bed reactor; conveying a flow of a first inert gas into the reaction chamber and contacting the catalyst; pre-heating the catalyst; conveying a flow of a feedstock gas into the reaction chamber and contacting the catalyst; heating the catalyst in the reaction chamber using microwave energy, thereby heating the feedstock gas and thereby converting at least a portion of the feedstock gas to higher hydrocarbons; wherein the fixed-bed reactor comprises an microwave energy apparatus configured to provide microwave energy to the reaction chamber of the fixed-bed reactor; wherein the reaction chamber is configured with a first entry port to provide a flow of a first inert gas to the reaction chamber; wherein the reaction chamber is configured with a second entry port to provide a flow of a feedstock gas to the reaction chamber; and wherein the feedstock gas comprises the natural gas and a second inert gas.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

FIG. 10A shows data obtained from a second cycle use for percent ethane conversion versus time-on-stream for the indicated catalyst. FIG. 10B shows data obtained from a fifth cycle use for percent ethane conversion versus time-on-stream for the indicated catalyst. FIG. 10C shows data obtained from average aromatic selectivity versus reaction cycle for the indicated catalyst.

FIGS. 11A-11D show representative data obtained using disclosed catalysts for the percent change in benzene concentration versus time-on-stream for each of five reaction cycles as indicated. FIG. 11A shows data obtained using a disclosed Mo catalyst the percent change in benzene concentration versus time-on-stream for each of five reaction cycles as indicated. FIG. 11B shows data obtained using a disclosed MoFe catalyst for the percent change in benzene concentration versus time-on-stream for each of five reaction cycles as indicated. FIG. 11C shows data obtained using a disclosed MoZn catalyst for the percent change in benzene concentration versus time-on-stream for each of five reaction cycles as indicated. FIG. 11D shows data obtained using a disclosed MoFeZn catalyst for the percent change in benzene concentration versus time-on-stream for each of five reaction cycles as indicated.

FIG. 12A shows data obtained using a disclosed Mo catalyst for total aromatic yields (toluene and benzene, as indicated) for each of five reaction cycles as indicated. FIG. 12B shows data obtained using a disclosed MoFe catalyst for total aromatic yields (toluene and benzene, as indicated) for each of five reaction cycles as indicated. FIG. 12C shows data obtained using a disclosed MoZn catalyst for total aromatic yields (toluene and benzene, as indicated) for each of five reaction cycles as indicated. FIG. 12D shows data obtained using a disclosed MoFeZn catalyst for total aromatic yields (toluene and benzene, as indicated) for each of five reaction cycles as indicated.

FIGS. 13A-13C show representative transmission electron micrograph (TEM) and electron dispersive spectroscopy (EDS) data pertaining to catalyst deactivation and regeneration. FIG. 13A shows a representative TEM image of a disclosed Mo catalyst with a spot (Spot 1) indicated. FIG. 13B shows a representative TEM image of a disclosed MoFe catalyst with spots (Spots 2 and 3) indicated. FIG. 13C shows representative EDS data obtained for each of the spots indicated in FIGS. 13A and 13B.

FIGS. 14A-14C show representative transmission electron micrograph (TEM) and electron dispersive spectroscopy (EDS) data pertaining to catalyst deactivation and regeneration. FIG. 14A shows a representative TEM image of a disclosed MoZn catalyst with spots (Spots 1 and 2) indicated. FIG. 14B shows a representative TEM image of a disclosed MoZn catalyst with spots (Spots 3 and 4) indicated. FIG. 14C shows representative EDS data obtained for each of the spots indicated in FIGS. 14A and 14B. In the figure, "N/F" stands for "not found."

FIGS. 15A-15C show representative transmission electron micrograph (TEM) and electron dispersive spectroscopy (EDS) data pertaining to catalyst deactivation and regeneration. FIG. 15A shows a representative TEM image of a disclosed MoFeZn catalyst with a spot (Spot 1) indicated. FIG. 15B shows a representative TEM image of a disclosed MoFeZn catalyst with spots (Spots 2 and 3) indicated. FIG. 15C shows representative EDS data obtained for each of the spots indicated in FIGS. 15A and 15B. In the figure, "N/F" stands for "not found."

FIGS. 16A-16D show representative temperature-programmed reduction (TPR) profile data obtained using representative disclosed catalysts as indicated prior to use ("fresh) and regenerated after a fifth cycle of use, e.g., "Mo" indicates that the data were obtained of a disclosed Mo catalyst, or after five cycles of use, e.g., "Mo-5Cyl" indicates a regenerated disclosed Mo catalyst after 5 cycles of use. FIG. 16A shows representative TPR obtained for a disclosed Mo catalyst in either an unused state (line for "Mo" in figure) or after regeneration after a fifth cycle of use (line for "Mo-5Cyl" in figure). FIG. 16B shows representative TPR obtained for a disclosed MoFe catalyst in either an unused state (line for "MoFe" in figure) or after regeneration after a fifth cycle of use (line for "MoFe-5Cyl" in figure). FIG. 16C shows representative TPR obtained for a disclosed MoZn catalyst in either an unused state (line for "MoZn" in figure) or after regeneration after a fifth cycle of use (line for "MoZn-5Cyl" in figure). FIG. 16D shows representative TPR obtained for a disclosed MoFeZn catalyst in either an unused state (line for "MoFeZn" in figure) or after regeneration after a fifth cycle of use (line for "MoFeZn-5Cyl" in figure).

FIG. 17A shows TPD profile data obtained for disclosed Mo catalyst. FIG. 17B shows TPD profile data obtained for disclosed MoFe catalyst. FIG. 17C shows TPD profile data obtained for disclosed MoZn catalyst. FIG. 17D shows TPD profile data obtained for disclosed MoFeZn catalyst. FIG. 17A shows TPD profile data obtained for a control zeolite catalyst (H/ZSM-5).

FIGS. 18A-18D show representative data obtained using disclosed catalysts for the percent change in toluene concentration versus time-on-stream (TOS) for the indicated catalyst for each of five reaction cycles (fresh, $1^{st}$, $2^{nd}$, $3^{rd}$, and $4^{th}$) as indicated. FIG. 18A shows data obtained using a disclosed Mo catalyst for the percent change in toluene concentration versus time-on-stream for each of five reaction cycles as indicated. FIG. 18B shows data obtained using a disclosed MoFe catalyst for the percent change in toluene concentration versus time-on-stream for each of five reaction cycles as indicated. FIG. 18C shows data obtained using a disclosed MoZn catalyst for the percent change in toluene concentration versus time-on-stream for each of five reaction cycles as indicated. FIG. 18D shows data obtained using a disclosed MoFeZn catalyst for the percent change in toluene concentration versus time-on-stream for each of five reaction cycles as indicated.

FIGS. 19A-19D show representative data obtained using disclosed catalysts for the percent change in hydrogen concentration versus time-on-stream (TOS) for the indicated catalyst for each of five reaction cycles (fresh, $1^{st}$, $2^{nd}$, $3^{rd}$, and $4^{th}$) as indicated. FIG. 19A shows data obtained using a disclosed Mo catalyst for the percent change in hydrogen concentration versus time-on-stream for each of five reaction cycles as indicated. FIG. 19B shows data obtained using a disclosed MoFe catalyst for the percent change in hydrogen concentration versus time-on-stream for each of five reaction cycles as indicated. FIG. 19C shows data obtained using a disclosed MoZn catalyst for the percent change in hydrogen concentration versus time-on-stream for each of five reaction cycles as indicated. FIG. 19D shows data obtained using a disclosed MoFeZn catalyst for the percent change in hydrogen concentration versus time-on-stream for each of five reaction cycles as indicated.

FIGS. 20A-20D show representative data obtained using disclosed catalysts for the percent change in methane concentration versus time-on-stream (TOS) for the indicated catalyst for each of five reaction cycles (fresh, $1^{st}$, $2^{nd}$, $3^{rd}$, and $4^{th}$) as indicated. FIG. 20A shows data obtained using a disclosed Mo catalyst for the percent change in methane concentration versus time-on-stream for each of five reaction cycles as indicated. FIG. 20B shows data obtained using a disclosed MoFe catalyst for the percent change in methane concentration versus time-on-stream for each of five reaction cycles as indicated. FIG. 20C shows data obtained using a disclosed MoZn catalyst for the percent change in methane concentration versus time-on-stream for each of five reaction cycles as indicated. FIG. 20D shows data obtained using a disclosed MoFeZn catalyst for the percent change in methane concentration versus time-on-stream for each of five reaction cycles as indicated.

Figure 1:
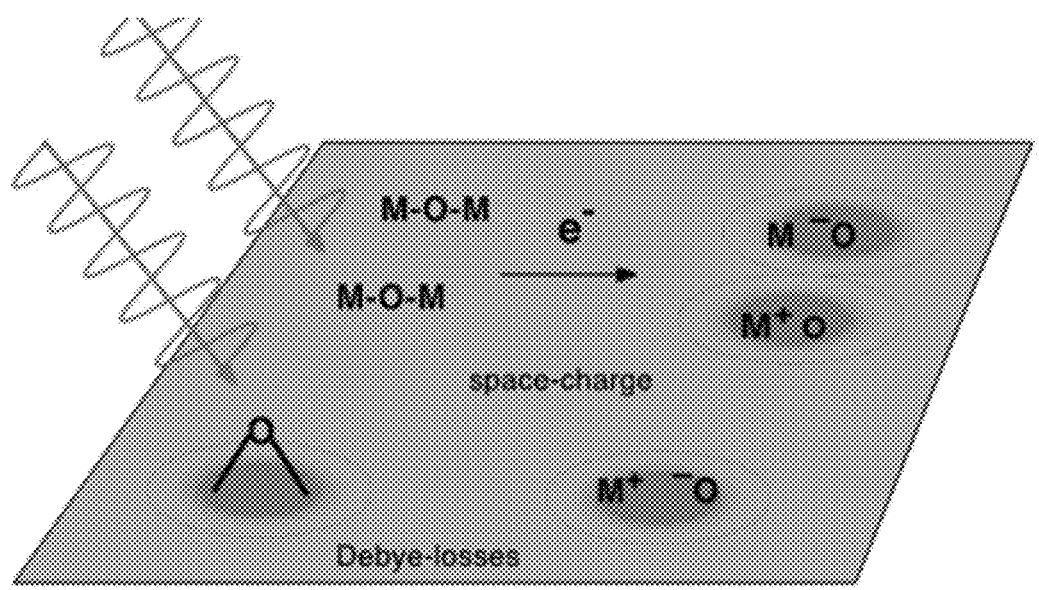
FIG. 1 shows a proposed reaction model for space-charge and Debye dielectric loss mechanisms for microwaves interacting with a catalyst surface for selective bond activation of reactant molecules.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, reference to a metal in a catalyst comprises reference to the recited metal in the zero oxidation or elemental state, as well as oxides of the same metal. For example, the catalyst metal or metals can be alternatively present in either form depending upon whether the catalyst has been reduced or oxidized, or even a mixture of forms, i.e., a mixture of reduced or elemental metal with the corresponding oxide(s). For example, the particular compositional mix of metal and metal oxides in a disclosed catalyst will be associated whether the catalyst is in a state prior to use the methods disclosed herein for the non-oxidative catalytic direct conversion of natural gas to higher order hydrocarbons or following use in such methods. In some instances, e.g., following calcination, a metal present in the catalyst can be in the form of the corresponding metal oxide, e.g., a catalyst comprising Pt, Mo, and Fe following calcination would comprise oxides such as $PtO_2$, $Mo_2O_3$, $Fe_2O_3$. However, during use in the non-oxidative catalytic direct conversion of natural gas, i.e., the catalytic reaction, $H_2$ is produced with concomitant reduction of a metal. In some instances, the method can comprise a pre-reduction step in which the catalyst is reduced prior to introduction of natural gas to the catalyst. Thus, a catalyst can begin in the form of metal oxide. It is understood that the oxidation state of a recited metal may be zero or in a lower valence tstate than the oxidation state of metals of the corresponding metal oxide. In some instances, the catalyst can comprise a mixture of a metal and the corresponding metal oxide(s) such that the mixture functions as an active phase of the catalyst. Thus, in some instances reference to a catalyst comprising a metal or metals is inclusive of a catalyst having both the given metal and metal oxide as promotors.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

B. Abbreviations

The following abbreviations are used herein throughout:
a) BET: Brunauer-Emmett-Teller (BET), e.g. Brunauer-Emmett-Teller (BET) model.
b) CNT: Carbon nanotube.
c) HR-TEM: High-Resolution Transmission Electron Microscopy.
d) ICP-OES: Inductively coupled plasma optical emission spectrometry.
e) SAR: Silica/alumina ratio.
f) SCD: Segmented-array charge-coupled device, e.g., as in a detector.
g) TEM: Transmission Electron Microscopy.
h) TGA: Thermogravimetric analysis.
i) TOS: Time-on-stream.
j) TPD: Temperature-programmed desorption.
k) TPO: Temperature-programmed oxidation.
l) TPR: Temperature-programmed reduction.
m) UHP: Ultra-high purity, e.g. as in chemical grade.
n) XRD: X-ray diffraction.

C. Catalyst Compositions

In accordance with the purpose(s) of the disclosure, as embodied and broadly described herein, the disclosure, in one aspect, relates to compositions for catalysts comprising a zeolite and a metal oxide. In some aspects, the metal oxide comprises a first metal oxide and a second metal oxide. In further aspects, the metal oxide comprises a mixture of two or more metal oxides. The zeolite used in the catalyst can be any suitable zeolite. In a further aspect, the zeolite is a pentasil zeolite. In a still further aspect, the zeolite is a ZSM-5 type zeolite.

Disclosed are heterogeneous catalysts comprising: a zeolite present in an amount of about 80 wt % to about 99.95 wt % based on the total weight of the catalyst; and a metal oxide present in an amount of about 0.05 wt % to about 20 wt % based on the total weight of the catalyst.

In various aspects, the disclosed heterogeneous catalyst is designed to interact with microwave radiation in the disclosed processes for direct, non-oxidative conversion of natural gas to higher hydrocarbons. For example, the disclosed heterogenerous catalysts comprise a metal material, such as a metal oxide, and a support material, such as a zeolite. In a further aspect, the zeolite is a pentasil zeolite material, e.g., a ZSM-5 type zeolite. The metal material in the disclosed heterogeneous catalysts can be highly dispersed on a high surface area support. In a still further aspect, the metal material can comprise a noble metal (e.g., Pt, Pd, Rh), a noble metal oxide, a noble metal salt, or combinations thereof; a transition metal (Ni, Co, Fe, Mo, etc), a transition metal oxide, a transition metal salt, or combinations thereof; or any combination of the foregoing. In various aspects, the disclosed heterogenous catalysts provide for catalysis, or catalytic reactions on active sites comprising a disclosed metal, metal oxide, metal salt, or combinations thereof. Without wishing to be bound by a particular theory, it is believed that electron sharing between reactant (methane) and active sites (metals) are steps in activation of the reactants. In a still further aspect, the metal, metal oxide, metal salt, or combinations thereof, in the disclosed heterogeneous catalysts are sensitive to electromagnetic energy. Without wishing to be bound by a particular theory, it is believed that the microwave energy in the disclosed processes carries electromagnetic energy onto metal sites directly, providing an electron shift between catalyst and reactant. Further, without wishing to be bound by a particular theory, it is believed that the microwave energy used in the disclosed process can directly activate methane via the chemical reaction: $CH4 \rightarrow CH4^*+e$, such that the electron deficient $CH4^*$ species can adsorb on active sites in the disclosed heterogeneous catalyst, thereby resulting in additional electron sharing and activation of the C—H bond. In various aspects, the disclosed heterogeneous catalysts are designed to be highly selective and efficient in terms of delivering energy to the active sites. Moreover, as discussed above, the disclosed heterogeneous catalysts are designed to interact with microwave energy, thus obviating the requirement for thermal transfer. In conventional reaction methods, a furnace is utilized to provide thermal energy, requiring transfer of heat from the furnace to the reaction chamber and from the reaction chamber to the catalyst support and from there to the metal materials, in terms of active sites, therein in order to catalyze a chemical reaction. The design of the disclosed heterogeneous catalysts allows for the direct interaction of microwave energy with the metal materials of the catalyst composition itself.

D. Processes for Preparing the Disclosed Heterogeneous Catalysts

In accordance with the purpose(s) of the disclosure, as embodied and broadly described herein, the present disclosure, in one aspect, relates to processes for making the disclosed heterogeneous catalysts comprising preparing a mixture of a zeolite and one or more metal salts. In some aspects, the preparation of the catalyst comprises aspects of incipient wetness impregnation.

Also disclosed are processes for synthezing a disclosed heterogeneous catalyst, the process comprising: forming a mixture comprising a zeolite and a metal salt solution, wherein the metal salt solution is present as an aqueous solution of a metal salt; wherein the zeolite is present in an amount of about 80 wt % to about 99.95 wt % based on the total weight of the zeolite powder and the metal salt; and wherein the metal salt is present in amount corresponding to about 0.05 wt % to about 20 wt % based on the total weight of the zeolite powder and the metal salt; heating the mixture of the zeolite and the metal salt solution, thereby forming a dried mixture comprising the zeolite and the metal salt; and calcining the dried mixture of the zeolite and metal salt.

Also disclosed are processes for synthezing a disclosed heterogeneous catalyst, the process comprising: forming a mixture comprising a zeolite and a metal salt solution, wherein the metal salt solution is present as an aqueous solution of a metal salt; wherein the zeolite is present in an amount of about 80 wt % to about 99.95 wt % based on the total weight of the zeolite powder and the metal salt; and wherein the metal salt is present in amount corresponding to about 0.05 wt % to about 20 wt % based on the total weight of the zeolite powder and the metal salt; heating the mixture of the zeolite and the metal salt solution, thereby forming a dried mixture comprising the zeolite and the metal salt; and calcining the dried mixture of the zeolite and metal salt.

In various aspects, the disclosed catalysts can be prepared by an incipient wetness impregnation method such as disclosed herein above.

In other aspects, the disclosed catalysts can be prepared by using a very dilute solution of a metal salt and/or organometallic in a solvent, such as less than about 0.05 $g/cm^3$, and soaking a disclosed zeolite with the very dilute solution of the metal salt and/or organometallic compound, followed by evaporation of the solvent, drying, and calcining. The solvent can comprise water, one or more organic solvents, or combinations thereof.

In other aspects, the disclosed catalysts can be prepared by using spray application methods comprising spraying a solution of a metal salt and/or organometallic in a solvent onto a disclosed zeolite, e.g., a disclosed zeolite arranged as a layer.

In other aspects, the disclosed catalysts can be prepared using chemical vapor deposition methods.

In other aspects, the disclosed catalysts can be prepared using a metal nano particle material, wherein the metal nanoparticle material is prepared using so-gel techniques, followed by adhering the metal containing so-gel onto a zeolite, then calcining the material in order to fix the metals onto the zeolite.

In various aspects, drying herein is understood to include a state wherein the catalyst is essentially dry, but nevertheless comprises some amount of solvent, such as water. That is, the material can be dry, but have solvent molecules present in the pore structure of the zeolite such that there are hydroxy (OH) groups and protons present on the surface of the zeolite. In some aspects, the zeolite material is dry when there is less then 5 wt % of solvent remaining associated with the zeolite.

In various aspects, the catalyst can be used in the disclosed methods for conversion of natural gas to higher hydrocarbons after the calcining step of the disclosed methods for preparation of the catalyst. Optionally, after the calcining step, the catalyst can be further process by a pre-reduction step wherein the catalyst is exposed to a flow of gas comprising hydrogen. The pre-reduction step can further comprise heating the catalyst in the presence of the gas flow.

E. Processes for Conversion of Natural Gas to Higher Hydrocarbons

In accordance with the purpose(s) of the disclosure, as embodied and broadly described herein, the present disclosure relates to methods for direct, non-oxidative preparation of higher hydrocarbons from natural gas. In a further aspect, the methods for preparation of higher hydrocarbons from natural gas are selective for high yield production of C6 and higher hydrocarbons. In the disclosed processes, it is understood that the processes, without wishing to be bound by a particular theory, can comprise integration of heterogeneous catalyst with microwave. That is, a disclosed catalyst by itself can catalyze the disclosed reaction, but in the absence of the use of microwave energy, the catalyst can deactivate and be rendered less effective than the disclosed process carried out in the presence microwave irradiation. In general, microwave irradiation of the feedstock gas by itself would not enable the disclosed reaction. Rather, without wishing to be bound by a particular theory, it believed that the integration, i.e., synergy, of the disclosed catalysts used to catalyze a reaction in the presence of microwave irradiation that renders the disclosed facile conversion of natural case to higher order hydrocarbons, including aromatic hydrocarbons.

Also disclosed are processes for conversion of natural gas to higher hydrocarbons, the process comprising arranging a disclosed heterogenous catalyst in a reaction chamber of a fixed-bed reactor; conveying a flow of a first inert gas into the reaction chamber and contacting the catalyst; pre-heating the catalyst; conveying a flow of a feedstock gas into the reaction chamber and contacting the catalyst; heating the catalyst in the reaction chamber using microwave energy, thereby heating the feedstock gas and thereby converting at least a portion of the feedstock gas to higher hydrocarbons; wherein the fixed-bed reactor comprises an microwave energy apparatus configured to provide microwave energy to the reaction chamber of the fixed-bed reactor; wherein the reaction chamber is configured with a first entry port to provide a flow of a first inert gas to the reaction chamber; wherein the reaction chamber is configured with a second entry port to provide a flow of a a feedstock gas to the reaction chamber; and wherein the feedstock gas comprises the natural gas and a second inert gas.

Figure 2:
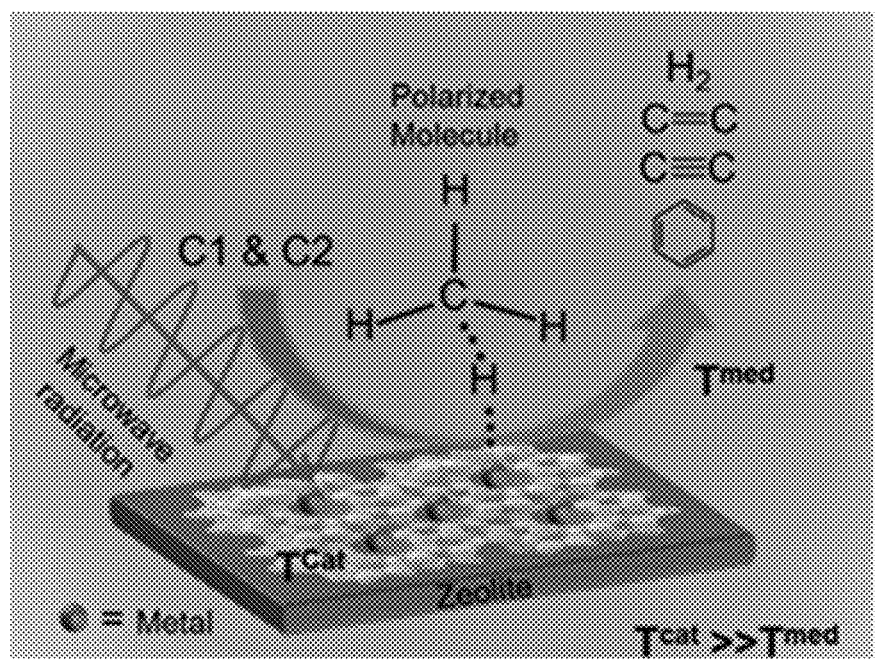
FIG. 2 shows a proposed reaction model for conversion of natural gas in the presence of a disclosed microwave sensitive catalyst.

In various aspects, the disclosed processes solves the challenges of the utilizing natural gas for production of higher hydrocarbon chemical feedstocks by providing processes and catalyst compositions that fundamentally change molecular activation process at interface of reactant (e.g., methane) and catalyst surface. Surprisingly, under low reaction severity (i.e., low temperature and ambient pressure), the disclosed heterogeneous catalysts can be used in processes that synergistically integrate microwave (or microwave plasma) reaction chemistry with novel disclosed heterogeneous catalysts that can selectively activate natural gas through microwave irradiation. Without wishing to be bound by a particular theory, a mechanism by which the catalyst and reacting species can interact with the microwave field and provide energy to the reaction is by relaxation processes, such as dipolar or Debye processes, which involve the coupling of the radiation with dipoles in the solid catalyst. As depicted in FIG. 1, such dipoles can be defect sites (i.e., atomic vacancies) in the catalysts or dangling bonds on the surface of catalysts. In various aspects, dipoles on the surface can be reactant or products that would be susceptible to selective bond activation effects, which in turn can affect reaction rates. FIG. 2 depicts a possible mechanism for methane conversion to aromatics, acetylene and ethylene. Without wishing to be bound by a particular theory, it is believed that the catalyst materials themselves have dielectric properties that allow them to absorb microwaves, especially at higher temperatures.

In a further aspect, a disclosed heterogeneous catalyst can further comprise a metal dopant, such as iron. Without wishing to be bound by a particular theory, it is believed that a disclosed heterogeneous catalyst further comprising a metal dopant, such as iron, could interact with the microwave through other mechanisms. That is, a ferromagnetic species could couple with the magnetic component of the microwave field, and accordingly providing additional energy into the catalyzed reaction.

In various aspects, the catalyst used in the conversion of natural gas to higher hydrocarbons can be regenerated. In a further aspect, regeneration provides a catalyst that has about 80% to about 100% of the activity of the catalyst prior to use in the conversion process. In some aspects, the catalyst can be regenerated by removal of coke formed on the catalyst during the conversion process. In further aspects, a catalyst can be regenerated by replishment of metal in the catalyst using a disclosed method of preparing a disclosed catalyst, e.g., incipient wetness impregnation can be used to replish metals in the catalyst following use in the disclosed conversion processes.

In a further aspect, without wishing to be bound by a particular aspect, the disclosed heterogenous catalysts, and the disclosed processes utilizing the catalyst, can have an additional mode of providing energy into the catalyzed reaction, via coupling of the microwave field with polar intermediate species on the surface of the catalyst, which are known to be strong microwave absorbers. Such coupling of the microwave field with polar intermediate species can further improve conversion efficiency and selectivity of the chemical reactions catalyzed by the disclosed heterogeneous catalysts.

In various aspects, without wishing to be bound by a particular theory, it is believed that in the disclosed processes, microwave energy can be selectively delivered to the interface between active sites and reaction intermediates without losing energy to the surrounding environment, therefore significantly improving energy efficiency. In the examples discussed herein below, it has been observed that microwave irradiation activates methane to form a plasma in the presence of the disclosed heterogeneous catalyst compositions compared to processes that do not utilize the catalysts or do not utilize microwave energy. That is, the disclosed processes utilizing the disclosed heterogeneous catalysts demonstrated enhanced conversion efficiencies and selectivity in the reaction products (i.e., greater selective production of C6 (i.e., benzene/toluene/xylene or BTX compounds) than reaction equilibrium theory would predict in a conventional system in thermal equilibrium (e.g., see FIG. 8 and the data in the Examples herein below).

In various aspects, without wishing to be bound by a particular theory, it is believed that in addition to activating active catalyst sites, the use of microwave frequency in the disclosed processes also directly activates natural gas molecules. Accordingly, in various aspects, the disclosed processes can be optimized in the appropriate selection of the microwave frequency used. That is, in a further aspect, increasing microwave frequency can provide for decreased energy transfer to the bulk volume with concomitant enhanced selectively of energy applied to the active sites. In a still further aspect, the disclosed processes utilized the disclosed heterogeneous catalysts can provide lower overall synthesis temperatures at higher microwave frequencies.

Figure 4:
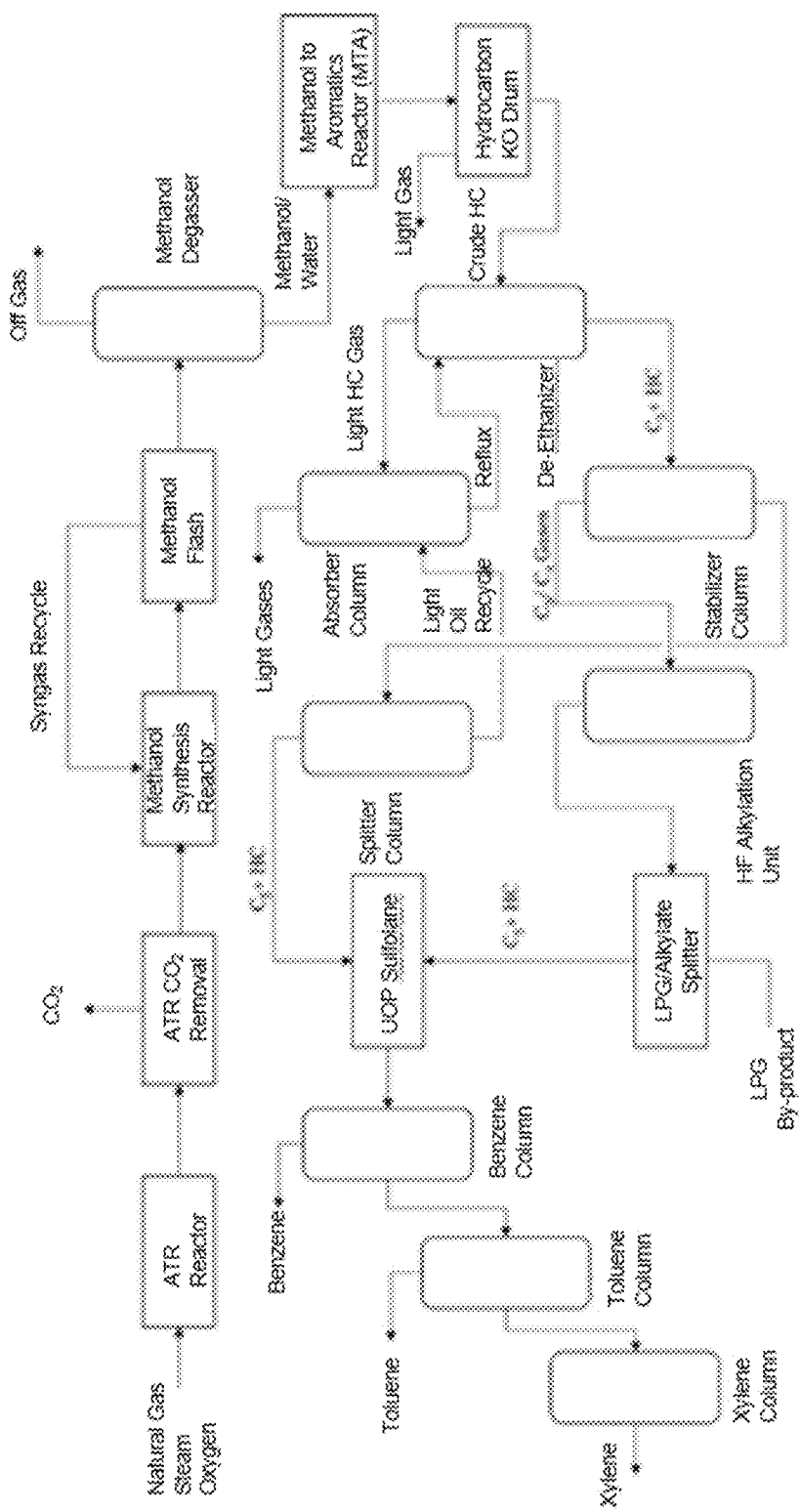
FIG. 4 shows a representative process flow diagram for indirect aromatics production from natural gas via conventional gas-to-liquid and methanol-to-aromatics production process.
Figure 5:
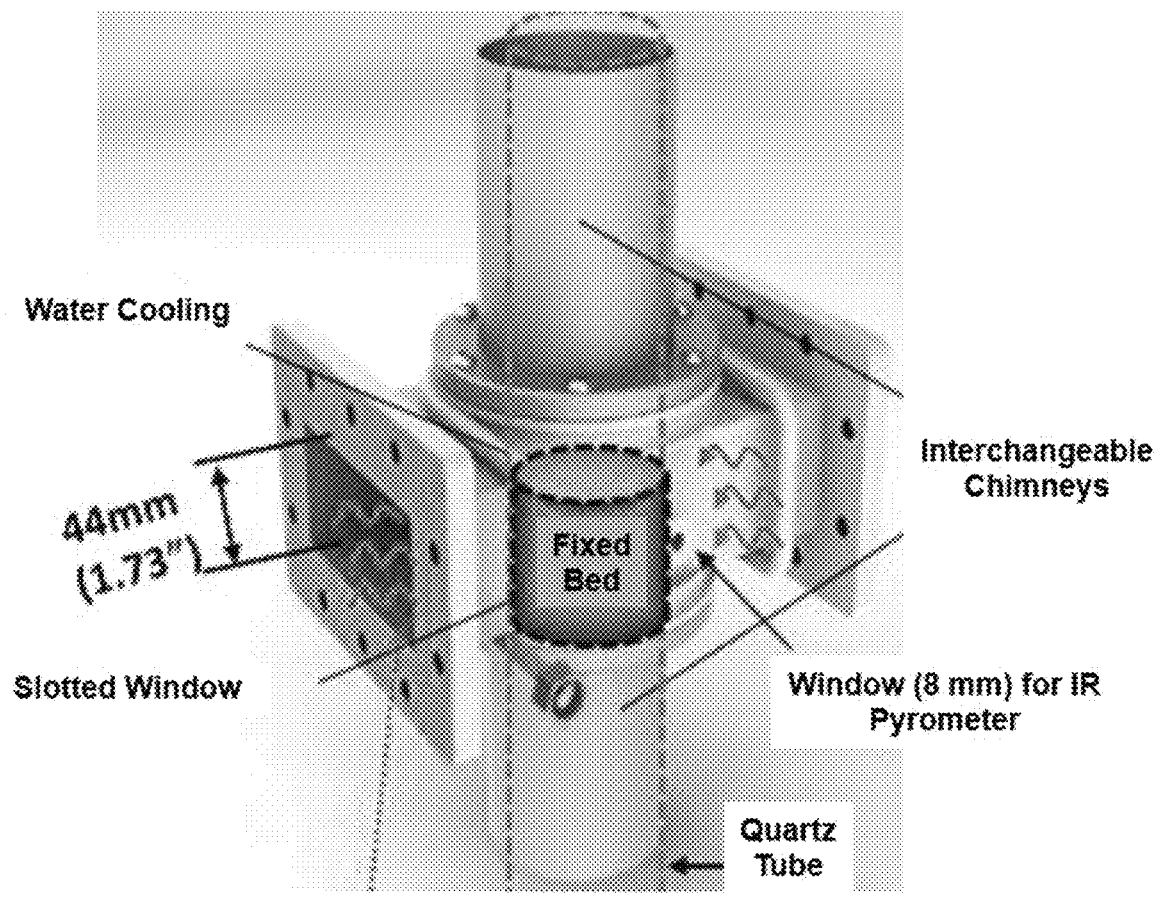
FIG. 5 shows a representative apparatus for carrying out a disclosed method of the disclosure.

In various aspects, the disclosed processes for direct, non-oxidative conversion of natural gas to higher hydrocarbons comprising use of the disclosed heterogeneous catalysts in the presence of microwave energy should enable the reduction of the number of unit operation. As depicted in the process flow diagrams in FIGS. 3 and 4, the process should be capable of realizing significant reductions in energy requirements and capital costs. In some aspects, the disclosed processes can utilize a fixed-bed reactor comprising a microwave energy apparatus configured to provide variable microwave frequency and energy output to the reaction chamber. Such a fixed-bed reactor is believed to be readily scalable to the particular requirements of a natural gas production site. FIG. 5 depicts a disclosed microwave reactor configuration showing aspects of delivery of microwave energy to a reaction chamber comprising a disclosed heterogenous catalyst over which would be conveyed a flow of natural gas. In some aspects, the natural gas can be mixed with an inert gas, such as helium, argon, nitrogen, or mixtures thereof.

In contrast, convention production of higher hydrocarbons, such as aromatics, from natural gas via indirect route are inefficient both in terms of the chemical reactions and capital. For example, recently built gas-to-liquid plants have cost tens of billions of dollars. Moreover, in such a gas-to-liquid process to synthesize aromatics, the indirect synthetic route typically comprise the following reaction steps:

Step 1: (syngas production):
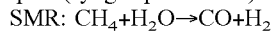
SMR: $CH_4+H_2O \rightarrow CO+H_2$
Partial Oxidation: $CH_4+O_2+H_2O \rightarrow CO+H_2$
Dry Reforming: $CH_4+CO_2 \rightarrow CO+H_2$ Step 2: (methanol synthesis):
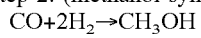
$CO+2H_2 \rightarrow CH_3OH$ Step 3: (methanol to aromatic synthesis):
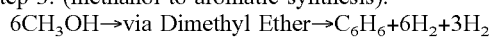
$6CH_3OH \rightarrow$ via Dimethyl Ether $\rightarrow C_6H_6+6H_2+3H_2$ Commercially available technologies for natural gas conversion to aromatics require multi-unit operations: syngas production, methanol synthesis, and methanol to aromatics (MTA). Accordingly, such conventional methods are capital intensive, chemically inefficient, and require significant energy inputs.

In contrast, theoretically a direct, non-oxidative methane conversion to aromatics could eliminate costly syngas production, resulting in capital savings and improvement in energy efficiency. However, thus far such methods suffer from significant technical issues that prohibit their commercial use. For example, a method for direct natural gas conversion to aromatics without requiring intermediate oxidative products such as methanol has been reported as follows:

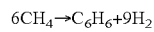
$6CH_4 \rightarrow C_6H_6+9H_2$

However, the reported process is thermodynamically limited, e.g., at reaction temperatures of about 700° C., a methane conversion of only about 10% was achieved. In order to further shift the equilibrium in the foregoing chemical to the desired product, even higher temperatures are necessary. However, use of higher temperatures is limited by significant side reactions, such as coking, which become dominate and lead to inevitable catalyst deactivation. Thus, although a direct conversion route is believed to be advantageous in chemical efficiency and capital cost, the foregoing demonstrates that heretofore it is not a commercially viable approach.

The disclosed processes utilizing application of microwave energy in the reaction comprising the disclosed heterogeneous catalysts surprisingly overcome the technical limitations of prior direct, non-oxidative routes to the conversion of natural gas to higher hydrocarbons. In particular, the predominant component of natural gas, methane, has a tetragonal structure that is difficult to activate, i.e., break the C—H bond. However, the disclosed processes utilizing the disclosed heterogeneous catalysts provide a surprisingly facile approach to selectively activate the C—H bond at low reaction severity that minimizes side reactions and increase conversion efficiencies.

Figure 3:
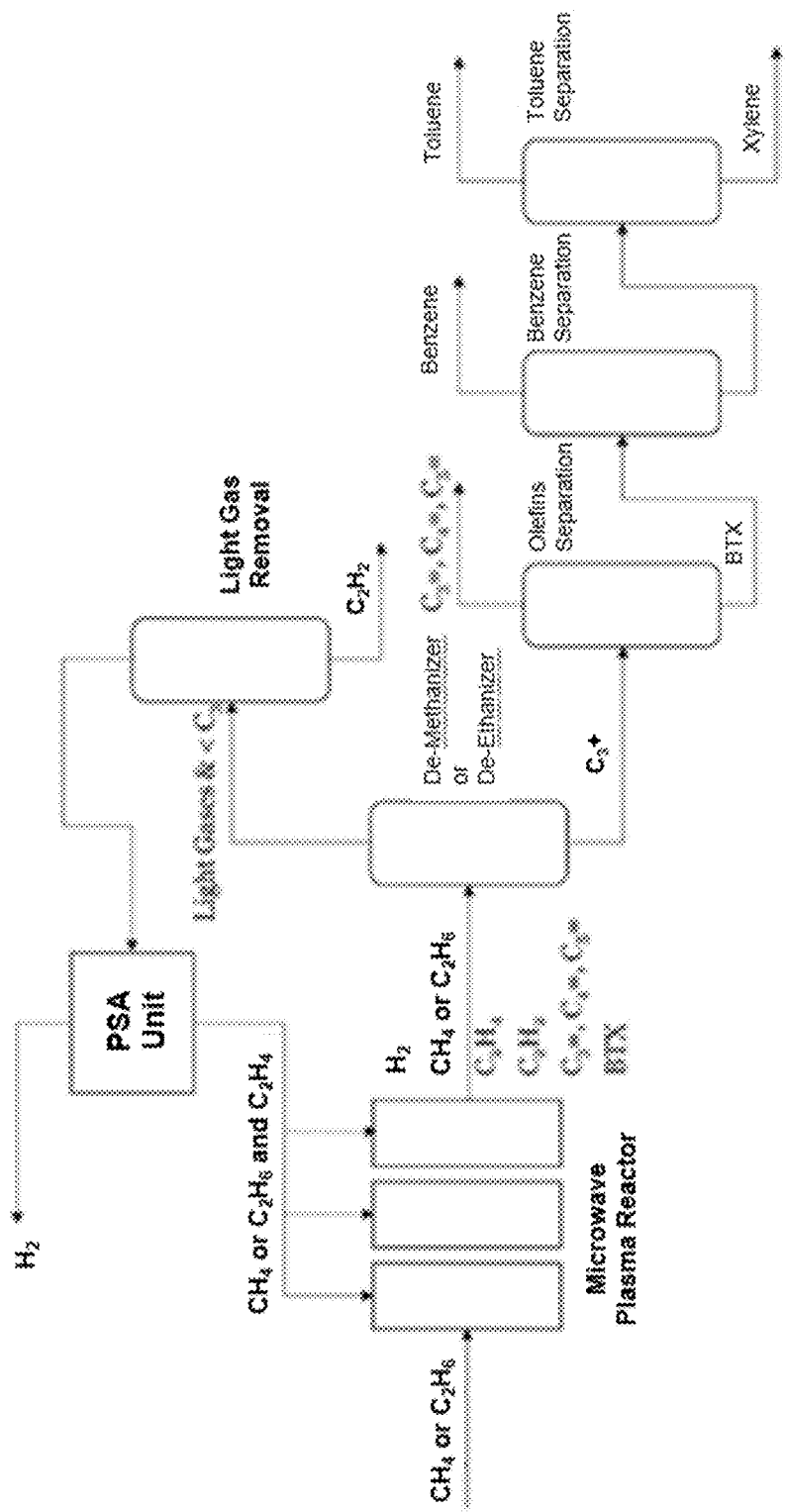
FIG. 3 shows a representative process flow diagram of a disclosed process for direct, non-oxidative aromatics production from natural gas using microwave catalysis technology.

Process simulation and technoeconomic analysis (TEA) of the disclosed methods were carried out to compare the microwave plasma catalytic proves for direct, non-oxidative methane conversion with indirect route that involves syngas production, methanol synthesis, followed by methanol-to-aromatics. FIGS. 3 and 4 show process flow diagrams of two potential scalable approaches utilized the disclosed processes. Table 1 below summarizes the TEA analysis where the microwave catalysis technology via direct route is compared with conventional indirect conversion process, and the data show significant potential reduction in unit operations. Specifically, the TEA presented in Table 1 compares, based on 5000 bpd output, the anticipated costs for production of higher hydrocarbons using a disclosed process for direct conversion of natural gas using microwave energy with a disclosed heterogeneous catalyst against the projects costs for similar production of higher hydrocarbons using an indirect conversion process via syngas as discussed above.

TABLE 1

|  | Direct, Non-Oxidative Microwave-Catalytic Process | Conventional Indirect Syngas Route via GTL and MTA |
|---|---|---|
| Total Direct Cost ($) | 61,981,300 | 126,590,000 |
| Non-MW Utility ($) | 12,902,232 | 39,288,665 |
| MW Electricity ($) | 1,475,365 |  |
| Raw Feed (kg/h) | 9,950 | 41,818 |
| Key Products (kg/h) |  |  |
| Benzene | 1,550 | 250 |
| Toluene | 1,043 | 1,025 |
| Xylene | 527 | 2,334 |

As shown in the TEA presented in Table 1, among the significant anticipated the advantages and impacts of the disclosed process compared to conventional indirect processes via a syngas are: (a) significant improvement in energy efficiency (63%) can be achieved due to elimination of syngas production, MW selective activation, no air separation, and higher carbon yield; and (b) greater than 51% capital cost reduction due to the reduction in the number of unit operation, increase in energy productivity by 4× due to improvement in feedstock efficiency, leading to an estimated >10× reduction in capacity cost ($/kg per day).

F. Aspects

The following listing of exemplary aspects supports and is supported by the disclosure provided herein.

Aspect 1. A heterogeneous catalyst comprising: a zeolite present in an amount of about 80 wt % to about 99.95 wt % based on the total weight of the catalyst; and a metal or metal oxide present in an amount of about 0.05 wt % to about 20 wt % based on the total weight of the catalyst.

Aspect 2. The catalyst of Aspect 1, wherein the zeolite is present in an amount of about 90 wt % to about 99.95 wt %.

Aspect 3. The catalyst of Aspect 1, wherein the zeolite is present in an amount of about 95 wt % to about 99.95 wt %.

Aspect 4. The catalyst of Aspect 1, wherein the zeolite is present in an amount of about 97 wt % to about 99.95 wt %.

Aspect 5. The catalyst of any one of Aspect 1-Aspect 4, wherein the zeolite has a pore size of at least about 3 Å.

Aspect 6. The catalyst of any one of Aspect 1-Aspect 4, wherein the zeolite has a pore size of at least about 5 Å.

Aspect 7. The catalyst of any one of Aspect 1-Aspect 6, wherein the zeolite has a $SiO_2/Al2O_3$ mole ratio of about 10 to about 250.

Aspect 8. The catalyst of any one of Aspect 1-Aspect 6, wherein the zeolite has a $SiO_2/Al2O_3$ mole ratio of about 10 to about 200.

Aspect 9. The catalyst of any one of Aspect 1-Aspect 6, wherein the zeolite has a $SiO_2/Al2O_3$ mole ratio of about 10 to about 150.

Aspect 10. The catalyst of any one of Aspect 1-Aspect 6, wherein the zeolite has a $SiO_2/Al2O_3$ mole ratio of about 10 to about 100.

Aspect 11. The catalyst of any one of Aspect 1-Aspect 6, wherein the zeolite has a $SiO_2/Al2O_3$ mole ratio of about 20 to about 80.

Aspect 12. The catalyst of any one of Aspect 1-Aspect 6, wherein the zeolite has a $SiO_2/Al2O_3$ mole ratio of about 20 to about 70.

Aspect 13. The catalyst of any one of Aspect 1-Aspect 6, wherein the zeolite has a $SiO_2/Al2O_3$ mole ratio of about 20 to about 60.

Aspect 14. The catalyst of any one of Aspect 1-Aspect 6, wherein the zeolite has a $SiO_2/Al2O_3$ mole ratio of about 30 to about 70.

Aspect 15. The catalyst of any one of Aspect 1-Aspect 6, wherein the zeolite has a $SiO_2/Al2O_3$ mole ratio of about 30 to about 60.

Aspect 16. The catalyst of any one of Aspect 1-Aspect 6, wherein the zeolite has a $SiO_2/Al2O_3$ mole ratio of about 40 to about 70.

Aspect 17. The catalyst of any one of Aspect 1-Aspect 6, wherein the zeolite has a $SiO_2/Al2O_3$ mole ratio of about 40 to about 60.

Aspect 18. The catalyst of any one of Aspect 1-Aspect 13, wherein the zeolite is a pentasil zeolite.

Aspect 19. The catalyst of any one of Aspect 1-Aspect 13, wherein the zeolite is a zeolite having a structure selected from: ZSM 3, ZSM-5, ZSM-11, ZSM-12, ZSM-20, ZSM-21, ZSM-22, ZSM-23, ZSM-35, ZSM 38, ZSM 43, ZSM-48, CSZ-1,PSH-3, mordenite, faujasite, mazzite, offretite, gmelinite, cancrinite, zeolite β, ferrierite, heulandite, zeolite ρ, ZSM 20, chabasite, and mixtures thereof.

Aspect 20. The catalyst of any one of Aspect 1-Aspect 19, wherein the zeolite is a zeolite having a structure of ZSM-5.

Aspect 21. The catalyst of any one of Aspect 1-Aspect 20, wherein the metal or metal oxide is present in an amount of about 0.05 wt % to about 10 wt %.

Aspect 22. The catalyst of any one of Aspect 1-Aspect 20, wherein the metal or metal oxide is present in an amount of about 0.05 wt % to about 5 wt %.

Aspect 23. The catalyst of any one of Aspect 1-Aspect 20, wherein the metal or metal oxide is present in an amount of about 0.05 wt % to about 3 wt %.

Aspect 24. The catalyst of any one of Aspect 1-Aspect 23, wherein the metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof.

Aspect 25. The catalyst of Aspect 24, wherein the metal or metal oxide is selected from molybdenum, palladium, platinum, tungsten, gallium, tin, and combinations thereof.

Aspect 26. The catalyst of Aspect 24, wherein the metal or metal oxide is selected from molybdenum, platinum, gallium, and combinations thereof.

Aspect 27. The catalyst of any one of Aspect 1-Aspect 26, wherein the metal or metal oxide comprises a first metal or metal oxide and a second metal oxide; wherein the first metal or metal oxide is present in an amount of about 0.05 wt % to about 10 wt %; and wherein the second metal or metal oxide is present in an amount of about 0.05 wt % to about 10 wt %, provided that the second metal or metal oxide is not the same as the first metal oxide.

Aspect 28. The catalyst of Aspect 27, wherein the first metal or metal oxide is present in an amount of about 0.05 wt % to about 7.5 wt %; and wherein the second metal or metal oxide is present in an amount of about 0.05 wt % to about 7.5 wt %.

Aspect 29. The catalyst of Aspect 27, wherein the first metal or metal oxide is present in an amount of about 0.05 wt % to about 5 wt %; and wherein the second metal or metal oxide is present in an amount of about 0.05 wt % to about 5 wt %.

Aspect 30. The catalyst of Aspect 27, wherein the first metal or metal oxide is present in an amount of about 0.05 wt % to about 4 wt %; and wherein the second metal or metal oxide is present in an amount of about 0.05 wt % to about 4 wt %.

Aspect 31. The catalyst of Aspect 27, wherein the first metal or metal oxide is present in an amount of about 0.05 wt % to about 3 wt %; and wherein the second metal or metal oxide is present in an amount of about 0.05 wt % to about 3 wt %.

Aspect 32. The catalyst of Aspect 27, wherein the first metal or metal oxide is present in an amount of about 0.05 wt % to about 3 wt %; and wherein the second metal or metal oxide is present in an amount of about 0.05 wt % to about 1 wt %.

Aspect 33. The catalyst of Aspect 27, wherein the first metal or metal oxide is present in an amount of about 0.05 wt % to about 3 wt %; and wherein the second metal or metal oxide is present in an amount of about 0.1 wt % to about 1 wt %.

Aspect 34. The catalyst of Aspect 27, wherein the first metal or metal oxide is present in an amount of about 0.05 wt % to about 3 wt %; and wherein the second metal or metal oxide is present in an amount of about 0.1 wt % to about 0.9 wt %.

Aspect 35. The catalyst of Aspect 27, wherein the first metal or metal oxide is present in an amount of about 0.05 wt % to about 3 wt %; and wherein the second metal or metal oxide is present in an amount of about 0.1 wt % to about 0.8 wt %.

Aspect 36. The catalyst of Aspect 27, wherein the first metal or metal oxide is present in an amount of about 0.05 wt % to about 3 wt %; and wherein the second metal or metal oxide is present in an amount of about 0.1 wt % to about 0.7 wt %.

Aspect 37. The catalyst of Aspect 27, wherein the first metal or metal oxide is present in an amount of about 0.05 wt % to about 3 wt %; and wherein the second metal or metal oxide is present in an amount of about 0.1 wt % to about 0.6 wt %.

Aspect 38. The catalyst of Aspect 27, wherein the first metal or metal oxide is present in an amount of about 0.05 wt % to about 3 wt %; and wherein the second metal or metal oxide is present in an amount of about 0.1 wt % to about 0.5 wt %.

Aspect 39. The catalyst of any one of Aspect 27-Aspect 38, wherein the first metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof; and wherein the second metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof, provided that the second metal or metal oxide is not the same as the first metal oxide.

Aspect 40. The catalyst of any one of Aspect 27-Aspect 38, wherein the first metal or metal oxide is selected from molybdenum, palladium, platinum, tungsten, gallium, tin, and combinations thereof; and wherein the second metal or metal oxide is selected from molybdenum, palladium, platinum, tungsten, gallium, tin, and combinations thereof.

Aspect 41. The catalyst of any one of Aspect 27-Aspect 38, wherein the first metal or metal oxide is selected from molybdenum, platinum, gallium, and combinations thereof; and wherein the second metal or metal oxide is selected from molybdenum, platinum, gallium, and combinations thereof.

Aspect 42. The catalyst of any one of Aspect 27-Aspect 38, wherein the first metal or metal oxide is selected from molybdenum, platinum, and combinations thereof; and wherein the second metal or metal oxide is an oxide of metal selected from iron, zinc, gallium, and combinations thereof.

Aspect 43. The catalyst of any one of Aspect 27-Aspect 38, wherein the first metal or metal oxide is selected from molybdenum, platinum, and combinations thereof; and wherein the second metal or metal oxide is an oxide of iron.

Aspect 44. The catalyst of any one of Aspect 27-Aspect 38, wherein the first metal or metal oxide is selected from molybdenum, platinum, and combinations thereof; and wherein the second metal or metal oxide is an oxide of zinc.

Aspect 45. The catalyst of any one of Aspect 27-Aspect 38, wherein the first metal or metal oxide is selected from molybdenum, platinum, and combinations thereof; and wherein the second metal or metal oxide is an oxide of gallium.

Aspect 46. The catalyst of any one of Aspect 27-Aspect 45, further comprising a third metal oxide, and wherein the third metal or metal oxide is present in an amount of about 0.05 wt % to about 10 wt %, provided that the third metal or metal oxide is not the same as the first metal or metal oxide or the second metal oxide.

Aspect 47. The catalyst of Aspect 46, wherein the third metal or metal oxide is present in an amount of about 0.05 wt % to about 7.5 wt %.

Aspect 48. The catalyst of Aspect 46, wherein the third metal or metal oxide is present in an amount of about 0.05 wt % to about 5 wt %.

Aspect 49. The catalyst of Aspect 46, wherein the third metal or metal oxide is present in an amount of about 0.05 wt % to about 4 wt %.

Aspect 50. The catalyst of Aspect 46, wherein the third metal or metal oxide is present in an amount of about 0.05 wt % to about 3 wt %.

Aspect 51. The catalyst of Aspect 46, wherein the third metal or metal oxide is present in an amount of about 0.05 wt % to about 1 wt %.

Aspect 52. The catalyst of Aspect 46, wherein the third metal or metal oxide is present in an amount of about 0.1 wt % to about 1 wt %.

Aspect 53. The catalyst of Aspect 46, wherein the third metal or metal oxide is present in an amount of about 0.1 wt % to about 0.9 wt %.

Aspect 54. The catalyst of Aspect 46, wherein the third metal or metal oxide is present in an amount of about 0.1 wt % to about 0.8 wt %.

Aspect 55. The catalyst of Aspect 46, wherein the third metal or metal oxide is present in an amount of about 0.1 wt % to about 0.7 wt %.

Aspect 56. The catalyst of Aspect 46, wherein the third metal or metal oxide is present in an amount of about 0.1 wt % to about 0.6 wt %.

Aspect 57. The catalyst of Aspect 46, wherein the first metal or metal oxide is present in an amount of about 0.05 wt % to about 3 wt %; and wherein the second metal or metal oxide is present in an amount of about 0.1 wt % to about 0.5 wt %.

Aspect 58. The catalyst of any one of Aspect 45-Aspect 57, wherein the third metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof, provided that the third metal or metal oxide is not the same as the first metal or metal oxide or the second metal oxide.

Aspect 59. The catalyst of Aspect 58, wherein the third metal or metal oxide is selected from iron, zinc, molybdenum, palladium, platinum, tungsten, gallium, tin, and combinations thereof.

Aspect 60. The catalyst of Aspect 58, wherein the third metal or metal oxide is selected from iron, zinc, molybdenum, platinum, gallium, and combinations thereof.

Aspect 61. The catalyst of Aspect 58, wherein the third metal or metal oxide is selected from iron, zinc, gallium, and combinations thereof.

Aspect 62. The catalyst of Aspect 58, wherein the third metal or metal oxide is iron.

Aspect 63. The catalyst of Aspect 58, wherein the third metal or metal oxide is zinc.

Aspect 64. The catalyst of Aspect 58, wherein the third metal or metal oxide is gallium.

Aspect 65. A process for synthesizing the heterogeneous catalyst of any one of Aspect 1-Aspect 64, the process comprising: forming a mixture comprising a zeolite and a metal solution, wherein the metal solution is comprises a metal present in a solvent; wherein the metal present in the solvent is an organometallic compound or a metal cation derived from a metal salt; wherein the zeolite is present in an amount of about 80 wt % to about 99.95 wt % based on the total weight of the zeolite powder and the metal; and wherein the metal salt is present in amount corresponding to about 0.05 wt % to about 20 wt % based on the total weight of the zeolite powder and the metal; heating the mixture of the zeolite and the metal salt solution, thereby forming a dried mixture comprising the zeolite and the metal salt; and calcining the dried mixture of the zeolite and metal salt.

Aspect 66. The process of Aspect 65, wherein the solvent in the metal solution comprises water, one or more organic solvents, or combinations thereof.

Aspect 67. The process of Aspect 66, wherein the solvent in the metal solution consists essentially of water.

Aspect 68. The process of Aspect 66, wherein the solvent in the metal solution consists essentially of one or more organic solvents.

Aspect 69. The process of any one of Aspect 65-Aspect 68, wherein the metal is present in the solvent at a concentration of about 0.05 g/cm3 to about 0.3 g/cm3.

Aspect 70. The process of any one of Aspect 65-Aspect 68, wherein the metal is present in the solvent at a concentration of about 0.05 g/cm3 to about 0.15 g/cm3.

Aspect 71. The process of any one of Aspect 65-Aspect 70, wherein the metal present in the metal solution is an organometallic compound.

Aspect 72. The process of any one of Aspect 65-Aspect 71, wherein the zeolite is present in an amount of about 90 wt % to about 99.95 wt %.

Aspect 73. The process of any one of Aspect 65-Aspect 71, wherein the zeolite is present in an amount of about 95 wt % to about 99.95 wt %.

Aspect 74. The process of any one of Aspect 65-Aspect 71, wherein the zeolite is present in an amount of about 97 wt % to about 99.95 wt %.

Aspect 75. The process of any one of Aspect 65-Aspect 74, wherein the zeolite has a pore size of at least about 3 Å.

Aspect 76. The process of any one of Aspect 65-Aspect 74, wherein the zeolite has a pore size of at least about 5 Å.

Aspect 77. The process of any one of Aspect 65-Aspect 76, wherein the zeolite has a $SiO_2/Al2O_3$ mole ratio of about 10 to about 200.

Aspect 78. The process of any one of Aspect 65-Aspect 76, wherein the zeolite has a $SiO_2/Al2O_3$ mole ratio of about 10 to about 150.

Aspect 79. The process of any one of Aspect 65-Aspect 76, wherein the zeolite has a $SiO_2/Al2O_3$ mole ratio of about 10 to about 100.

Aspect 80. The process of any one of Aspect 65-Aspect 76, wherein the zeolite has a $SiO_2/Al2O_3$ mole ratio of about 20 to about 80.

Aspect 81. The process of any one of Aspect 65-Aspect 76, wherein the zeolite has a $SiO_2/Al2O_3$ mole ratio of about 30 to about 70.

Aspect 82. The process of any one of Aspect 65-Aspect 76, wherein the zeolite has a $SiO_2/Al2O_3$ mole ratio of about 40 to about 60.

Aspect 83. The process of any one of Aspect 65-Aspect 82, wherein the zeolite is a pentasil zeolite.

Aspect 84. The process of any one of Aspect 65-Aspect 82, wherein the zeolite is a zeolite having a structure selected from: ZSM 3, ZSM-5, ZSM-11, ZSM-12, ZSM-20, ZSM-21, ZSM-22, ZSM-23, ZSM-35, ZSM 38, ZSM 43, ZSM-48, CSZ-1,PSH-3, mordenite, faujasite, mazzite, offretite, gmelinite, cancrinite, zeolite β, ferrierite, heulandite, zeolite ρ, ZSM 20, chabasite, and mixtures thereof.

Aspect 85. The process of any one of Aspect 65-Aspect 84, wherein the zeolite is a zeolite having a structure of ZSM-5.

Aspect 86. The process of any one of Aspect 65-Aspect 85, wherein the zeolite is a calcined zeolite.

Aspect 87. The process of Aspect 86, further comprising calcining the zeolite.

Aspect 88. The process of Aspect 87, wherein the calcining the zeolite comprises heating the zeolite at a temperature of about 200° C. to about 700° C.

Aspect 89. The process of Aspect 87, wherein the calcining the zeolite comprises heating the zeolite at a temperature of about 300° C. to about 600° C.

Aspect 90. The process of Aspect 87, wherein the calcining the zeolite comprises heating the zeolite at a temperature of about 400° C. to about 600° C.

Aspect 91. The process of Aspect 87, wherein the calcining the zeolite comprises heating the zeolite at a temperature of about 450° C. to about 550° C.

Aspect 92. The process of any one of Aspect 87-Aspect 91, wherein the calcining is carried out for a period of about 0.5 hours to about 12 hours Aspect 93. The process of any one of Aspect 87-Aspect 91, wherein the calcining is carried out for a period of about 1 hour to about 6 hours Aspect 94. The process of any one of Aspect 87-Aspect 91, wherein the calcining is carried out for a period of about 1 hour to about 6 hours Aspect 95. The process of any one of Aspect 87-Aspect 91, wherein the calcining is carried out for a period of about 2 hour to about 4 hours Aspect 96. The process of any one of Aspect 86-Aspect 95, wherein the zeolite is an ammonium zeolite; and wherein the calcining the zeolite forms a protonated form of the zeolite.

Aspect 97. The process of any one of Aspect 65-Aspect 96, wherein the metal or metal oxide is present in an amount of about 0.05 wt % to about 10 wt %.

Aspect 98. The process of any one of Aspect 65-Aspect 96, wherein the metal or metal oxide is present in an amount of about 0.05 wt % to about 5 wt %.

Aspect 99. The process of any one of Aspect 65-Aspect 96, wherein the metal or metal oxide is present in an amount of about 0.05 wt % to about 3 wt %.

Aspect 100. The process of any one of Aspect 65-Aspect 99, wherein the metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof.

Aspect 101. The process of Aspect 100, wherein the metal or metal oxide is selected from molybdenum, palladium, platinum, tungsten, gallium, tin, and combinations thereof.

Aspect 102. The process of Aspect 100, wherein the metal or metal oxide is selected from molybdenum, platinum, gallium, and combinations thereof.

Aspect 103. The process of any one of Aspect 65-Aspect 102, wherein the metal or metal oxide comprises a first metal or metal oxide and a second metal oxide; wherein the first metal or metal oxide is present in an amount of about 0.05 wt % to about 10 wt %; and wherein the second metal or metal oxide is present in an amount of about 0.05 wt % to about 10 wt %, provided that the second metal or metal oxide is not the same as the first metal oxide.

Aspect 104. The process of Aspect 103, wherein the first metal or metal oxide is present in an amount of about 0.05 wt % to about 7.5 wt %; and wherein the second metal or metal oxide is present in an amount of about 0.05 wt % to about 7.5 wt %.

Aspect 105. The process of Aspect 103, wherein the first metal or metal oxide is present in an amount of about 0.05 wt % to about 5 wt %; and wherein the second metal or metal oxide is present in an amount of about 0.05 wt % to about 5 wt %.

Aspect 106. The process of Aspect 103, wherein the first metal or metal oxide is present in an amount of about 0.05 wt % to about 4 wt %; and wherein the second metal or metal oxide is present in an amount of about 0.05 wt % to about 4 wt %.

Aspect 107. The catalyst of Aspect 103, wherein the first metal or metal oxide is present in an amount of about 0.05 wt % to about 3 wt %; and wherein the second metal or metal oxide is present in an amount of about 0.05 wt % to about 3 wt %.

Aspect 108. The catalyst of Aspect 103, wherein the first metal or metal oxide is present in an amount of about 0.05 wt % to about 3 wt %; and wherein the second metal or metal oxide is present in an amount of about 0.05 wt % to about 1 wt %.

Aspect 109. The catalyst of Aspect 103, wherein the first metal or metal oxide is present in an amount of about 0.05 wt % to about 3 wt %; and wherein the second metal or metal oxide is present in an amount of about 0.1 wt % to about 1 wt %

Aspect 110. The catalyst of Aspect 103, wherein the first metal or metal oxide is present in an amount of about 0.05 wt % to about 3 wt %; and wherein the second metal or metal oxide is present in an amount of about 0.1 wt % to about 0.9 wt %.

Aspect 111. The catalyst of Aspect 103, wherein the first metal or metal oxide is present in an amount of about 0.05 wt % to about 3 wt %; and wherein the second metal or metal oxide is present in an amount of about 0.1 wt % to about 0.8 wt %.

Aspect 112. The catalyst of Aspect 103, wherein the first metal or metal oxide is present in an amount of about 0.05 wt % to about 3 wt %; and wherein the second metal or metal oxide is present in an amount of about 0.1 wt % to about 0.7 wt %.

Aspect 113. The catalyst of Aspect 103, wherein the first metal or metal oxide is present in an amount of about 0.05 wt % to about 3 wt %; and wherein the second metal or metal oxide is present in an amount of about 0.1 wt % to about 0.6 wt %.

Aspect 114. The catalyst of Aspect 103, wherein the first metal or metal oxide is present in an amount of about 0.05 wt % to about 3 wt %; and wherein the second metal or metal oxide is present in an amount of about 0.1 wt % to about 0.5 wt %.

Aspect 115. The process of any one of Aspect 103-Aspect 114, wherein the first metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof; and wherein the second metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof, provided that the second metal or metal oxide is not the same as the first metal oxide.

Aspect 116. The process of any one of Aspect 103-Aspect 114, wherein the first metal or metal oxide is selected from molybdenum, palladium, platinum, tungsten, gallium, tin, and combinations thereof; and wherein the second metal or metal oxide is selected from molybdenum, palladium, platinum, tungsten, gallium, tin, and combinations thereof.

Aspect 117. The process of any one of Aspect 103-Aspect 114, wherein the first metal or metal oxide is selected from molybdenum, platinum, gallium, and combinations thereof; and wherein the second metal or metal oxide is selected from molybdenum, platinum, gallium, and combinations thereof.

Aspect 118. The process of any one of Aspect 103-Aspect 114, wherein the first metal or metal oxide is selected from molybdenum, platinum, and combinations thereof; and wherein the second metal or metal oxide is an oxide of metal selected from iron, zinc, gallium, and combinations thereof.

Aspect 119. The process of any one of Aspect 103-Aspect 114, wherein the first metal or metal oxide is selected from molybdenum, platinum, and combinations thereof; and wherein the second metal or metal oxide is an oxide of iron.

Aspect 120. The process of any one of Aspect 103-Aspect 114, wherein the first metal or metal oxide is selected from molybdenum, platinum, and combinations thereof; and wherein the second metal or metal oxide is an oxide of zinc.

Aspect 121. The process of any one of Aspect 103-Aspect 114, wherein the first metal or metal oxide is selected from molybdenum, platinum, and combinations thereof; and wherein the second metal or metal oxide is an oxide of gallium.

Aspect 122. The process of any one of Aspect 103-Aspect 121, further comprising a third metal oxide, and wherein the third metal or metal oxide is present in an amount of about 0.05 wt % to about 10 wt %, provided that the third metal or metal oxide is not the same as the first metal or metal oxide or the second metal oxide.

Aspect 123. The process of Aspect 122, wherein the third metal or metal oxide is present in an amount of about 0.05 wt % to about 7.5 wt %.

Aspect 124. The process of Aspect 122, wherein the third metal or metal oxide is present in an amount of about 0.05 wt % to about 5 wt %.

Aspect 125. The process of Aspect 122, wherein the third metal or metal oxide is present in an amount of about 0.05 wt % to about 4 wt %.

Aspect 126. The process of Aspect 122, wherein the third metal or metal oxide is present in an amount of about 0.05 wt % to about 3 wt %.

Aspect 127. The process of Aspect 122, wherein the third metal or metal oxide is present in an amount of about 0.05 wt % to about 1 wt %.

Aspect 128. The process of Aspect 122, wherein the third metal or metal oxide is present in an amount of about 0.1 wt % to about 1 wt %.

Aspect 129. The process of Aspect 122, wherein the third metal or metal oxide is present in an amount of about 0.1 wt % to about 0.9 wt %.

Aspect 130. The process of Aspect 122, wherein the third metal or metal oxide is present in an amount of about 0.1 wt % to about 0.8 wt %.

Aspect 131. The process of Aspect 122, wherein the third metal or metal oxide is present in an amount of about 0.1 wt % to about 0.7 wt %.

Aspect 132. The process of Aspect 122, wherein the third metal or metal oxide is present in an amount of about 0.1 wt % to about 0.6 wt %.

Aspect 133. The process of Aspect 122, wherein the first metal or metal oxide is present in an amount of about 0.05 wt % to about 3 wt %; and wherein the second metal or metal oxide is present in an amount of about 0.1 wt % to about 0.5 wt %.

Aspect 134. The process of Aspect 122-Aspect 133, wherein the third metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof, provided that the third metal or metal oxide is not the same as the first metal or metal oxide or the second metal oxide.

Aspect 135. The process of Aspect 134, wherein the third metal or metal oxide is selected from iron, zinc, molybdenum, palladium, platinum, tungsten, gallium, tin, and combinations thereof.

Aspect 136. The process of Aspect 134, wherein the third metal or metal oxide is selected from iron, zinc, molybdenum, platinum, gallium, and combinations thereof.

Aspect 137. The process of Aspect 134, wherein the third metal or metal oxide is selected from iron, zinc, gallium, and combinations thereof.

Aspect 138. The process of Aspect 134, wherein the third metal or metal oxide is iron.

Aspect 139. The process of Aspect 134, wherein the third metal or metal oxide is zinc.

Aspect 140. The process of Aspect 134, wherein the third metal or metal oxide is gallium.

Aspect 141. The process of any one of Aspect 65-Aspect 118, wherein the heating the mixture of the zeolite and the metal salt solution is for a time sufficient such that the dried mixture comprising the zeolite and the metal salt is essentially free of water.

Aspect 142. The process of any one of Aspect 65-Aspect 118, wherein the heating the mixture of the zeolite and the metal salt solution is for a time sufficient such that the dried mixture comprising the zeolite and the metal salt has less than about 5 wt % water based on the total weight of the dried mixture.

Aspect 143. The process of any one of Aspect 65-Aspect 142, wherein the heating the mixture of the zeolite and the metal salt solution is carried out at a temperature of about 70° C. to about 200° C.

Aspect 144. The process of any one of Aspect 65-Aspect 142, wherein the heating the mixture of the zeolite and the metal salt solution is carried out at a temperature of about 90° C. to about 150° C.

Aspect 145. The process of any one of Aspect 65-Aspect 142, wherein the heating the mixture of the zeolite and the metal salt solution is carried out at a temperature of about 95° C. to about 105° C.

Aspect 146. The process of any one of Aspect 143-Aspect 145, wherein the heating is carried out for a period of about 1 hour to about 48 hours.

Aspect 147. The process of any one of Aspect 143-Aspect 145, wherein the heating is carried out for a period of about 6 hours to about 24 hours.

Aspect 148. The process of any one of Aspect 143-Aspect 145, wherein the heating is carried out for a period of about 6 hours to about 18 hours.

Aspect 149. The process of any one of Aspect 143-Aspect 145, wherein the heating is carried out for a period of about 6 hours to about 12 hours.

Aspect 150. The process of any one of Aspect 65-Aspect 149, wherein the calcining the dried mixture of the zeolite and metal salt is carried out at a temperature of about 300° C. to about 800° C.

Aspect 151. The process of any one of Aspect 65-Aspect 149, wherein the calcining the dried mixture of the zeolite and metal salt is carried out at a temperature of about 400° C. to about 700° C.

Aspect 152. The process of any one of Aspect 65-Aspect 149, wherein the calcining the dried mixture of the zeolite and metal salt is carried out at a temperature of about 400° C. to about 600° C.

Aspect 153. The process of any one of Aspect 65-Aspect 149, wherein the calcining the dried mixture of the zeolite and metal salt is carried out at a temperature of about 500° C. to about 700° C.

Aspect 154. The process of any one of Aspect 65-Aspect 149, wherein the calcining the dried mixture of the zeolite and metal salt is carried out at a temperature of about 500° C. to about 600° C.

Aspect 155. The process of any one of Aspect 150-Aspect 154, wherein the calcining the dried mixture of the zeolite and metal salt is carried out for a period of about 0.5 hours to about 24 hours.

Aspect 156. The process of any one of Aspect 150-Aspect 154, wherein the calcining the dried mixture of the zeolite and metal salt is carried out for a period of about 1 hour to about 24 hours.

Aspect 157. The process of any one of Aspect 150-Aspect 154, wherein the calcining the dried mixture of the zeolite and metal salt is carried out for a period of about 3 hours to about 24 hours.

Aspect 158. The process of any one of Aspect 150-Aspect 154, wherein the calcining the dried mixture of the zeolite and metal salt is carried out for a period of about 3 hours to about 18 hours.

Aspect 159. The process of any one of Aspect 150-Aspect 154, wherein the calcining the dried mixture of the zeolite and metal salt is carried out for a period of for about 3 hours to about 6 hours.

Aspect 160. The process of any one of Aspect 65-Aspect 159, further comprising pre-reduction of the catalyst in the presence of a flow of a gas comprising hydrogen gas.

Aspect 161. A process for conversion of natural gas to higher hydrocarbons, the process comprising arranging the catalyst of any one of Aspect 1-Aspect 64 or the catalyst made by the process of any one of Aspect 65-Aspect 160 in a reaction chamber of a reactor; conveying a flow of a first inert gas or a reducing gas into the reaction chamber and contacting the catalyst; pre-heating the catalyst in the reaction chamber using microwave energy; conveying a flow of a feedstock gas into the reaction chamber and contacting the catalyst; reacting the feedstock gas on the catalyst, thereby converting at least a portion of the feedstock gas to higher hydrocarbons; wherein the reactor comprises an microwave energy apparatus configured to provide microwave energy to the reaction chamber of the reactor; wherein the reaction chamber is configured to allow a continuous flow of a feedstock gas to the reaction chamber; and wherein the feedstock gas comprises natural gas comprising C1-C6 alkanes.

Aspect 162. The process of Aspect 161, wherein the reactor is a fixed-bed reactor.

Aspect 163. The process of Aspect 161, wherein the reactor is a moving-bed reactor.

Aspect 164. The process of any one of Aspect 161-Aspect 163, wherein the first inert gas is helium, argon, nitrogen, or combinations thereof.

Aspect 165. The process of Aspect 164, wherein the first inert gas is helium.

Aspect 166. The process of any one of Aspect 161-Aspect 165, wherein the flow of the first inert gas is about 10 ml/min to about 200 ml/min.

Aspect 167. The process of any one of Aspect 161-Aspect 165, wherein the flow of the first inert gas is about 20 ml/min to about 100 ml/min.

Aspect 168. The process of any one of Aspect 161-Aspect 165, wherein the flow of the first inert gas is about 30 ml/min to about 100 ml/min.

Aspect 169. The process of any one of Aspect 161-Aspect 165, wherein the flow of the first inert gas is about 30 ml/min to about 70 ml/min.

Aspect 170. The process of any one of Aspect 161-Aspect 169, wherein the pre-heating the catalyst is carried out at a catalyst heating temperature of about 300° C. to about 1000° C.

Aspect 171. The process of any one of Aspect 161-Aspect 169, wherein the pre-heating the catalyst is carried out at a catalyst heating temperature of about 400° C. to about 900° C.

Aspect 172. The process of any one of Aspect 161-Aspect 169, wherein the pre-heating the catalyst is carried out at a catalyst heating temperature of about 500° C. to about 800° C.

Aspect 173. The process of any one of Aspect 161-Aspect 169, wherein the pre-heating the catalyst is carried out at a catalyst heating temperature of about 600° C. to about 800° C.

Aspect 174. The process of any one of Aspect 161-Aspect 169, wherein the pre-heating the catalyst is carried out at a catalyst heating temperature of about 600° C. to about 700° C.

Aspect 175. The process of any one of Aspect 170-Aspect 174, wherein the heating rate is about 1° C./min to about 30° C./min until reaching the catalyst heating temperature.

Aspect 176. The process of any one of Aspect 170-Aspect 174, wherein the heating rate is about 5° C./min to about 20° C./min until reaching the catalyst heating temperature.

Aspect 177. The process of any one of Aspect 170-Aspect 174, wherein the heating rate is about 7° C./min to about 15° C./min until reaching the catalyst heating temperature.

Aspect 178. The process of any one of Aspect 170-Aspect 174, wherein the heating rate is about 8° C./min to about 12° C./min until reaching the catalyst heating temperature.

Aspect 179. The process of any one of Aspect 170-Aspect 178, wherein the pre-heating the catalyst is maintained at the catalyst heating temperature for a period of about 15 min to about 240 min.

Aspect 180. The process of any one of Aspect 170-Aspect 178, wherein the pre-heating the catalyst is maintained at the catalyst heating temperature for a period of about 30 min to about 180 min.

Aspect 181. The process of any one of Aspect 170-Aspect 178, wherein the pre-heating the catalyst is maintained at the catalyst heating temperature for a period of about 60 min to about 120 min.

Aspect 182. The process of any one of Aspect 161-Aspect 181, wherein the feedstock gas comprises about 5 vol % to about 100 vol % of the natural gas and about 0 vol % to about 90 vol % of a second inert gas.

Aspect 183. The process of Aspect 182, wherein the feedstock gas comprises about 10 vol % to about 70 vol % of the natural gas and about 30 vol % to about 90 vol % of the second inert gas.

Aspect 184. The process of Aspect 182, wherein the feedstock gas comprises about 20 vol % to about 50 vol % of the natural gas and about 50 vol % to about 80 vol % of the second inert gas.

Aspect 185. The process of Aspect 182, wherein the feedstock gas comprises about 20 vol % to about 40 vol % of the natural gas and about 60 vol % to about 80 vol % of the second inert gas.

Aspect 186. The process of any one of Aspect 182-Aspect 185, wherein the second inert gas is helium, argon, nitrogen, or combinations thereof.

Aspect 187. The process of Aspect 186, wherein the second inert gas is helium.

Aspect 188. The process of any one of Aspect 182-Aspect 187, wherein the first inert gas and the second inert gas have essentially the same composition.

Aspect 189. The process of any one of Aspect 161-Aspect 188, wherein the natural gas comprises one or more C1-C6 alkanes.

Aspect 190. The process of any one of Aspect 161-Aspect 189, wherein the natural gas comprises about 70 vol % to about 100 vol % methane.

Aspect 191. The process of Aspect 190, wherein the natural gas comprises about 70 vol % to about 95 vol % methane.

Aspect 192. The process of any one of Aspect 161-Aspect 191, wherein the first inert gas is helium, argon, nitrogen, or combinations thereof.

Aspect 193. The process of Aspect 192, wherein the first inert gas is helium.

Aspect 194. The process of any one of Aspect 161-Aspect 193, wherein the flow of the feedstock gas is about 10 ml/min to about 200 ml/min per gram of the catalyst.

Aspect 195. The process of any one of Aspect 161-Aspect 193, wherein the flow of the feedstock gas is about 20 ml/min to about 100 ml/min per gram of the catalyst.

Aspect 196. The process of any one of Aspect 161-Aspect 193, wherein the flow of the feedstock gas is about 30 ml/min to about 100 ml/min per gram of the catalyst.

Aspect 197. The process of any one of Aspect 161-Aspect 193, wherein the flow of the feedstock gas is about 30 ml/min to about 70 ml/min per gram of the catalyst.

Aspect 198. The process of any one of Aspect 161-Aspect 197, wherein about 5 vol % to about 90 vol % of the natural gas is converted to the higher hydrocarbons.

Aspect 199. The process of any one of Aspect 161-Aspect 197, wherein about 10 vol % to about 90 vol % of the natural gas is converted to the higher hydrocarbons.

Aspect 200. The process of any one of Aspect 161-Aspect 197, wherein about 30 vol % to about 80 vol % of the natural gas is converted to the higher hydrocarbons.

Aspect 201. The process of any one of Aspect 161-Aspect 197, wherein about 40 vol % to about 75 vol % of the natural gas is converted to the higher hydrocarbons.

Aspect 202. The process of any one of Aspect 161-Aspect 197, wherein about 10 vol % to about 90 vol % of the natural gas is converted to the aromatic hydrocarbons comprising a mixture of benzene, toluene, xylene, and C9 or greater aromatic compounds.

Aspect 203. The process of any one of Aspect 161-Aspect 197, wherein about 30 vol % to about 80 vol % of the natural gas is converted to the aromatic hydrocarbons comprising a mixture of benzene, toluene, xylene, and C9 or greater aromatic compounds.

Aspect 204. The process of any one of Aspect 161-Aspect 197, wherein about 40 vol % to about 75 vol % of the natural gas is converted to the aromatic hydrocarbons comprising a mixture of benzene, toluene, xylene, and C9 or greater aromatic compounds.

Aspect 205. The process of any one of Aspect 161-Aspect 204, wherein about 10 wt % to about 90 wt % of the higher hydrocarbons comprise C6 or higher hydrocarbons.

Aspect 206. The process of any one of Aspect 161-Aspect 204, wherein about 20 wt % to about 80 wt % of the higher hydrocarbons comprise C6 or higher hydrocarbons.

Aspect 207. The process of any one of Aspect 161-Aspect 204, wherein about 30 wt % to about 70 wt % of the higher hydrocarbons comprise C6 or higher hydrocarbons.

Aspect 208. The process of any one of Aspect 205-Aspect 207, wherein about 10 wt % to about 90 wt % of the C6 or higher hydrocarbons comprise a mixture of benzene, toluene, and xylene.

Aspect 209. The process of any one of Aspect 161-Aspect 204, wherein about 20 wt % to about 80 wt % of the C6 or higher hydrocarbons comprise a mixture of benzene, toluene, and xylene.

Aspect 210. The process of any one of Aspect 161-Aspect 204, wherein about 30 wt % to about 70 wt % of the C6 or higher hydrocarbons comprise a mixture of benzene, toluene, and xylene.

Aspect 211. The process of any one of Aspect 161-Aspect 210, wherein the heating the reaction chamber is using microwave energy having at a frequency of from about 0.9 MHz to about 90 GHz.

Aspect 212. The process of Aspect 211, wherein the heating the reaction chamber is using microwave energy having at a frequency of from about 1 MHz to about 50 GHz.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

G. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Catalyst Synthesis: Ammonium ZSM-5 zeolite powder with $SiO_2/Al_2O_3$ mole ratio (SAR) of 50 was obtained from Zeolyst Inc. ( ). Ammonium heptamolybdate tetrahydrate $((NH_4)_6Mo_7O_{24}\cdot4H_2O)$; gallium nitrate hydrate $Ga(NO_3)_3\cdot xH_2O$; and chloroplatinic acid hexahydrate $H_2PtCl_6\cdot6H_2O$ were obtained from Fischer Scientific. Briefly, the ammonium ZSM-5 zeolite powder was calcined at 500° C. in air for 3 h to convert the powder from the ammonium form to its protonated form (HZSM-5). Conventional incipient wetness impregnation was used to prepare Mo, Ga, Pt and GaPt catalysts. Typically, gallium nitrate hydrate salt corresponding to 3 wt % Ga was dissolved in deionized water and was added drop wise to HZSM-5 and the mixture was kept for 12 h for drying at 100° C. The powder was then calcined in air at 550° C. Molybdenum catalyst was also prepared following the same way as gallium. Similarly Pt promoted gallium catalysts was prepared by co-impregnation method. Compositional details of prepared catalysts, including the metallic concentration, are provided in Table 2 below.

TABLE 2

| Catalyst | Ga wt % | Pt wt % | Mo wt % |
| --- | --- | --- | --- |
| Mo/HZSM-5 | 0 | 0 | 3 |
| Ga/HZSM-5 | 3 | 0 | 0 |
| GaPt/HZSM-5 | 2.5 | 0.5 | 0 |
| Pt/HZSM-5 | 0 | 0.5 | 0 |

Catalyst Characterization: Powder X-ray diffraction analysis was performed on a PANalytical X'Pert Pro X-ray diffraction working under 45 kV and 40 mA using Cu Kα radiation. The 2θ angles were scanned from 5° to 50° (2θ). An X'celerator solid-state detector with a scan speed of 4.8° $min^{-1}$ was employed. Nitrogen adsorption/desorption isotherms were acquired using a Micromeritics ASAP-2020 unit. The program consisting of both adsorption and desorption branches typically ran at −196° C. after the sample was degassed at 300° C. for 3 h once the final temperature had been maintained. The specific surface area was calculated via the BET model. The $H_2$-temperature-programmed reduction ($H_2$-TPR) was carried out to study reducibility of the catalysts with Micromeritics Autochem 2950. The catalyst (100 mg) was pretreated at 100° C. under argon flow (50 mL/min) for 1 h and then cooled to 50° C. TPR was performed from 50° C. to 900° C. with a ramping rate of 10° C./min under 10% $H_2$ in argon (50 mL) flow. Temperature programmed desorption of ammonia ($NH_3$-TPD) was conducted using Micromeritics ASAP-2020 unit. Prior to each TPD run catalyst (200 mg) was dried at 500° C. for 30 minute with pure He (50 mL/min). Then catalyst was allowed to cool down at room temperature and final weight was taken. Catalyst was heated up again to 150° C. at a ramp of 10° C./min and exposed to 30 mL/min of 15% $NH_3$ in He for 35 minutes. Then catalyst was purged with pure He for 30 minutes to remove excess $NH_3$ before starting temperature ramp up to 750° C. (5° C./min,) to get the $NH_3$ desorption profile. Temperature programmed oxidation (TPO) was performed with 30 mg spent catalyst under a flow of 50 mL (10% $O_2$ in He) mixture by heating from room temperature to 750° C. with a rate of 10° C./min with a thermal conductivity detector in Micromeritics Autochem 2950. A JEOL TEM 2100 electron microscope operating at 200 kV was used for TEM sample observations. Samples for TEM were prepared by evaporating a droplet of dispersed catalyst in isopropanol onto a nickel mesh 200 grid.

Figure 6:
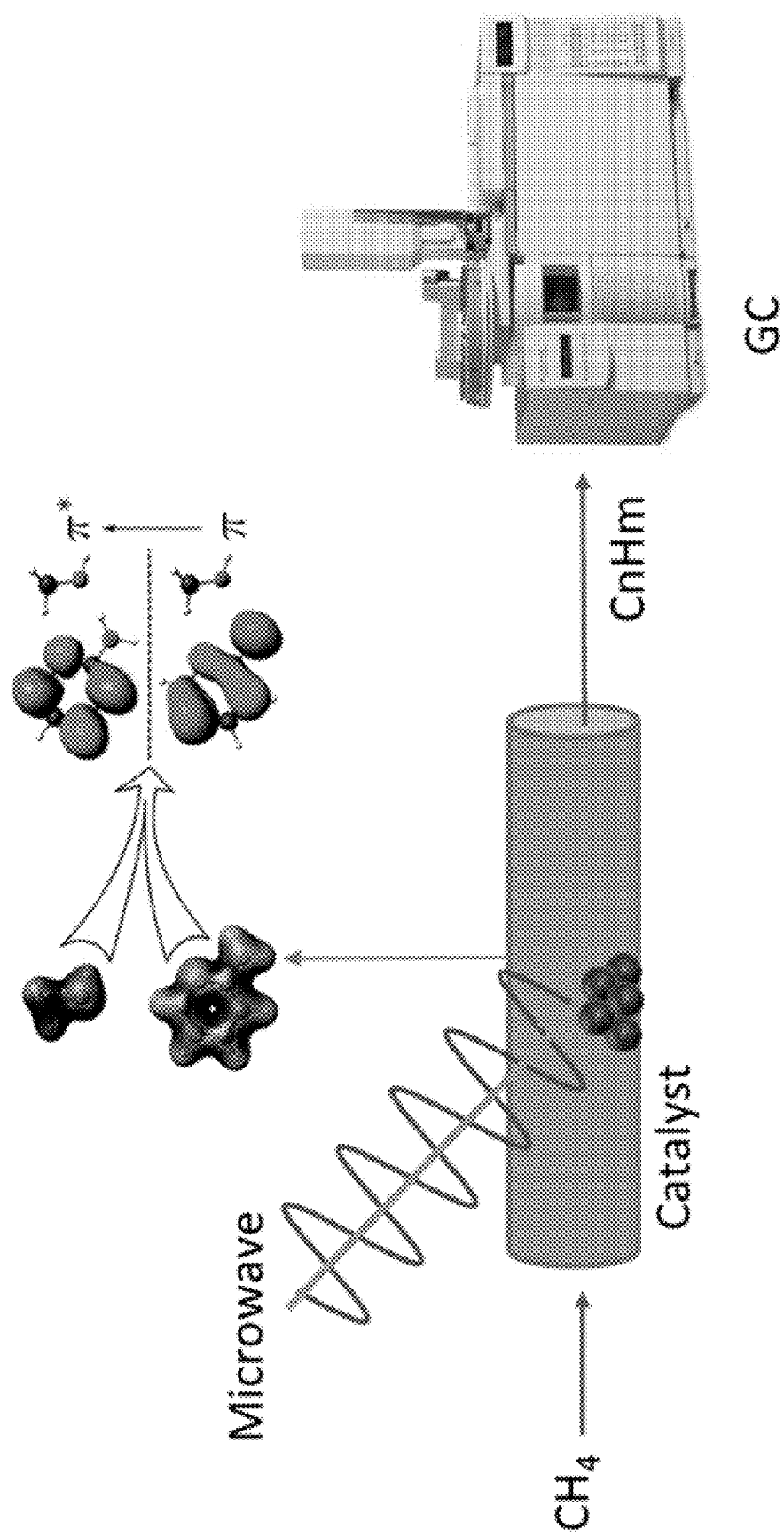
FIG. 6 shows a representative schematic of the testing procedure utilized to assess the non-oxidative conversion of natural gas to various compounds.
Figure 7:
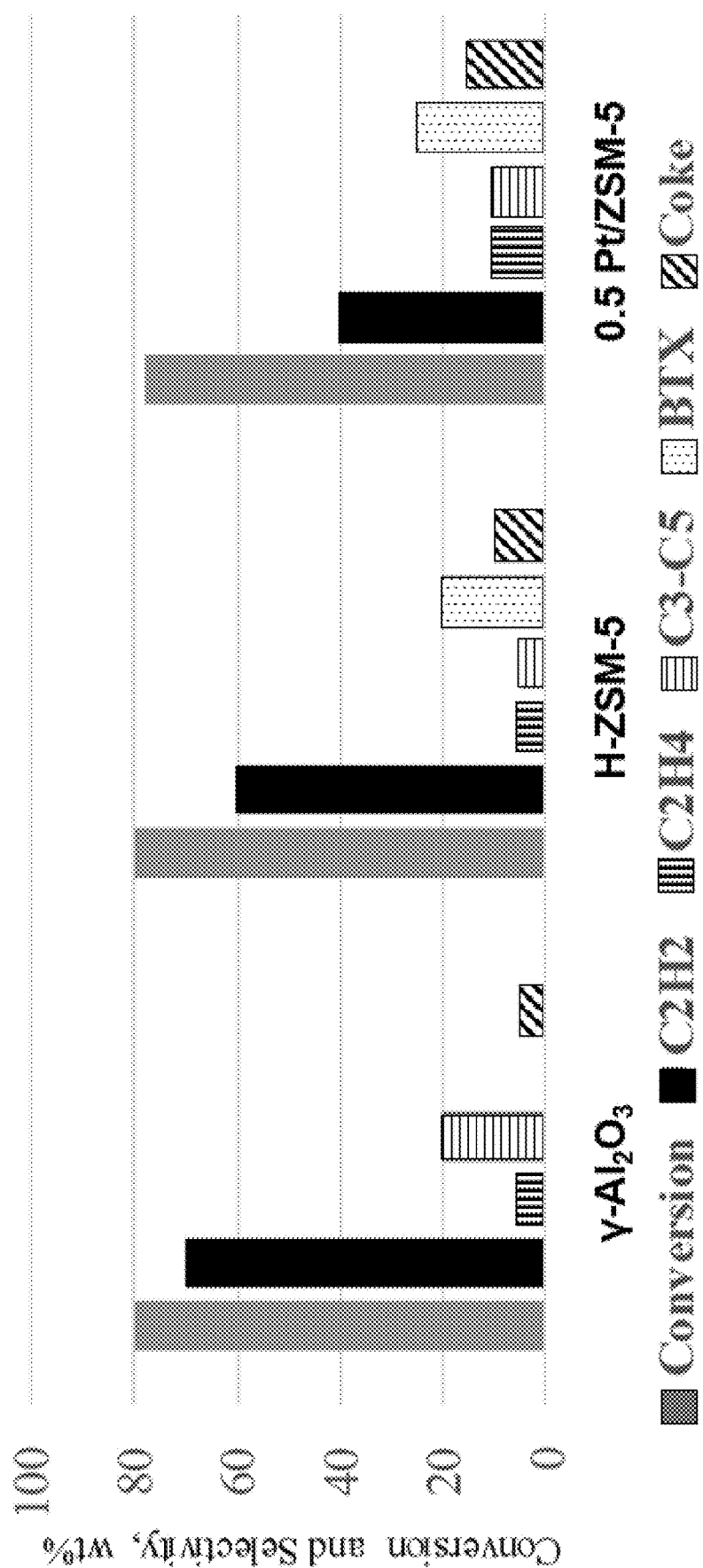
FIG. 7 shows representative data for conversion of natural gas using a disclosed process demonstrating the conversion and selectivity efficiencies of the disclosed process.

Catalytic Study: The reaction was carried out as depicted in FIG. 6. Briefly, the reaction was carried out in microwave plasma reactor connected with an Inficon Micro Gas Chromatography (Micro GC). In the experiment, about 1-2 grams of catalyst was loaded into a ½ inch diameter quartz tube and placed into the microwave unit. The temperature of the catalyst system was monitored by built-in IR sensor. A variable-frequency modulation (VFM) controller is applied to control the temperature, applied power and microwave frequency of the system. A sliding short and two EH tuners were adjusted manually to maximize the coupling of microwave power to the catalyst. The pressure of the reactor was at ambient pressure. The flow rate of feed gas was controlled by external mass flow controllers. The reaction was operated in continuous flow fixed-bed configuration. Before the reaction, the catalyst was heated in helium flow (50 mL/min) to 650° C. with a heating rate of 10° C./min and kept at this temperature for 90 min. Then the feed consisting of 30 vol. % $C_2H_6$+70 vol. % He was introduced with a flow rate 50 mL/min. Helium was used as an internal standard to account for the changes of ethane flow rate due to the reaction. The product gas, including aromatics, olefins, paraffins is analyzed and quantified by Micro GC as discussed below. Results for conversion of feed to higher hydrocarbons is shown in FIG. 7, and Table 3 below.

TABLE 3

| | $CH_4$ Conversion wt % | Product Selectivity, wt % | | | |
| --- | --- | --- | --- | --- | --- |
| | | Benzene | Ethylene | Naphthalene | Acetylene |
| Equilibrium (700° C.) | 9.8 | 54 | 6 | 40 | 0 |
| Microwave plasma catalysis (700° C.) | 78 | 25 | 10 | 25 | 40 |

Product Analysis: Benzene, toluene and hydrogen were analyzed using Pfeiffer Omnistar mass spectrometer (MS) connected with the reactor. Amount of naphthalene produced in this reaction was not accounted. Mass spectrometer was calibrated with the appropriate standard gas mixtures. Conversion of ethane was calculated based on hydrogen balance of the reaction. Also conversion of ethane and selectivity of products are calculated on mole % and wt % (hydrocarbon) basis, respectively.

Microwave plasma catalytic reactor testing procedure: The reaction was carried out in microwave plasma reactor connected with an Inficon Micro Gas Chromatography (Micro GC). In the experiment, about 1-2 grams of catalyst was loaded into a ½ inch diameter quartz tube and placed into the microwave unit. The temperature of the catalyst system was monitored by built-in IR sensor. A variable-frequency modulation (VFM) controller was applied to control the temperature, applied power and microwave frequency of the system.

A sliding short and two EH tuners were adjusted manually to maximize the coupling of microwave power to the catalyst. The pressure of the reactor was ambient pressure. The flow rate of feed gas was controlled by external mass flow controllers. The reaction was operated in continuous flow fixed-bed configuration. The product gas, including aromatics, olefins, and paraffins were analyzed and quantified by Micro GC.

Example 2

Catalyst Preparation: NH4-ZSM-5 zeolite catalyst with a silica/alumina ratio (SAR) of 23 was purchased from Zeolyst, Inc. Ammonium heptamolybdate tetrahydrate, zinc nitrate hexahydrate, and iron(II) chloride, anhydrous, were purchased from Acros Organics. The zeolite catalyst was first calcined at 500° C. in air for 3 h to convert NH4-ZSM-5 to H-ZSM-5. The conventional incipient wetness technique was used to prepare the Mo/ZSM-5 catalyst, while MoFe, MoZn, and MoFeZn on ZSM-5 were prepared by the coimpregnation method. After drying the catalysts at 105° C. for 5 h, the powders were calcined in air at 550° C. for 10 h. The chemical compositions of the prepared catalysts are shown in Table 4 below.

TABLE 4*

| Catalyst | Fresh | | | Spent** | | | Change | | |
| --- | --- | --- | --- | --- | --- | --- | --- | --- | --- |
| | Mo | Fe | Zn | Mo | Fe | Zn | Mo | Fe | Zn |
| Mo | 3.26 | | | 3.09 | | | 0.17 | | |
| MoFe | 3.39 | 0.43 | | 3.12 | 0.31 | | 0.27 | 0.12 | |
| MoZn | 3.44 | | 0.46 | 3.03 | | 0.22 | 0.41 | | 0.24 |
| MoFeZn | 3.36 | 0.45 | 0.44 | 3.17 | 0.37 | 0.21 | 0.19 | 0.08 | 0.23 |

*Amounts given in wt %.
**"Spent" catalyst = regenerated fifth cycle catalyst

Catalyst Characterization Methods: Powder XRD analysis was performed on a PANalytical X'Pert Pro (PW3040) set to 45 kV and 40 mA. Samples were scanned from 5° to 35° (2θ) using Cu Kα radiation. Highscore Plus Analyses software supplied by PANalyticial was used for data analysis.

Surface area analysis was carried out in a Micromeritics ASAP 2020 unit. The catalyst samples were degassed at 300° C. for 10 h under vacuum to remove any surface moisture and absorbed gases. Nitrogen was used as the adsorption gas. The surface area was calculated using the Brunauer-Emmett-Teller (BET) model, and the t-plot method was used to calculate micropore volume and micropore area.

NH$_3$-TPD experiments were carried out using a Micromeritics Autochem 2910 equipped with a thermal conductivity detector. The samples were heated to 300° C. at 5° C./min for 60 min under an inert flow of He to remove moisture and then cooled to 150° C. Premixed 15% ammonia in helium then flowed over the catalyst for 30 min at 30 mL/min. A baseline was determined by flowing helium over the sample for 30 min at 50 mL/min to remove weekly bounded ammonia from the catalyst surface. The samples were then heated to 700° C. at 5°/min.

Transmission electron microscopy (TEM) micrographs and energy-dispersive spectroscopy (EDS) analysis were obtained using a JEOL JEM-2100, equipped with Oxford EDS. The samples were prepared by sonicating in isopropyl alcohol for 10 min and then loaded onto a copper grid. The prepared TEM sample grids were dried in air for 8 h.

Catalyst Evaluation Methods: The reaction was carried out in a Micromeritics Autochem 2950 analyzer connected with a micro gas chromatograph (micro-GC) for gas analysis. For each experiment, 200 mg of catalyst was loaded into a quartz tube reactor. The reaction was carried out under atmospheric pressure and continuous flow conditions. The catalyst was heated to 615° C. in argon at a flow rate of 50 mL/min with the heating rate of 10° C./min. Pure ethane was mixed with argon to create a 36% ethane mixture, which then flowed over the catalyst at 50 mL/min. After 21 min of reaction, helium was introduced to purge ethane in the system. The catalyst remained at 615° C., where it was regenerated for 95 min in a flow of 2% oxygen in helium. After catalyst regeneration, helium was introduced to purge remaining oxygen in the system and the catalyst was ready for the next 21 min reaction cycle. A total of five reaction cycles (1 fresh and 4 regenerated) were performed for each catalyst. All reactant gases were purchased from AirGas with ultrahigh-purity (UHP) grade.

The reactant gases were analyzed by a four-channel Agilent 3000 micro-GC. The micrometrics unit internal valves and line temperatures were maintained at 150° C., and a 150-170° C. heated trace line attached to the inlet of the micro-GC was used to maintain the products in gas form. The micro-GC was equipped with four columns consisting of molecular sieve, PLOT U, aluminum, and OV-1, allowing for the analysis of hydrogen, methane, argon, ethane, ethylene, benzene, and toluene. Xylene was not traced, and naphthalene was separated out of the analysis stream; thus, concentrations were not reported. The ethane conversion and product selectivity were defined in equations 1 and 2, respectively.

$$\text{conversion (\%)} = \frac{\text{ethane fed (\%)} - \text{ethane out (\%)}}{\text{ethane fed (\%)}} \quad (1)$$

$$\text{selectivity of aromatics (\%)} = \frac{\text{benzene (\%)} \times 6 + \text{toluene (\%)} \times 7}{[\text{ethane fed (\%)} - \text{ethane out (\%)}] \times 2} \times 100 \quad (2)$$

TPO analyses were carried out on the coked catalyst using a Micrometrics Autochem 2950 equipped with a thermal conductivity detector. About 100 mg of coked catalyst was first heated to 300° C. with a ramp rate of 5° C./min in an inert flow of argon at 30 mL/min for 60 min. The sample was then cooled to ambient temperature, where it was then heated in the presence of 2% oxygen at a ramp rate of 2° C./min.

TGA of the coked catalyst was carried out using a TA Instrument SDT 650. The sample was heated to 150° C. for 60 min under an inert flow of helium to dry the sample. The sample was then heated from 150 to 700° C. in a flow of 2% oxygen. The temperature was then held constant for 30 min in 2% oxygen to ensure complete removal of the coke in the temperature range.

TPR was carried out in a Micrometrics AutoChem 2950 equipped with a thermal conductivity detector. The samples were heated to 300° C. at 10° C./min for 60 min under an inert flow of He to remove moisture and then cooled to 100° C. Premixed 10% hydrogen in argon was then flowed for 20 min over the catalyst for 25 mL/min to achieve a baseline. Once a baseline was achieved, the samples were heated to 900° C. at 5° C./min.

All trace metals were analyzed using ICP-OES on an Optima 7300 DV (PerkinElmer, Waltham, Mass., U.S.A.), which is a dual-view spectrometer with solid-state segmented-array charge coupled device (SCD) detectors. Calibration standards were purchased from Inorganic Ventures (Christiansburg, Va., U.S.A.) and are traceable to National Institute of Standards and Technology (NIST) standard reference materials. Fe, Mo, and Zn were measured after digestion in aqua regia acid. A total of 12 mg of each sample was digested in 12 mL of aqua regia (9 mL of HCl and 3 mL of $HNO_3$) acid and then further diluted 100-fold using a mixture of high-purity 2% nitric acid prior to analysis.

Figure 8:
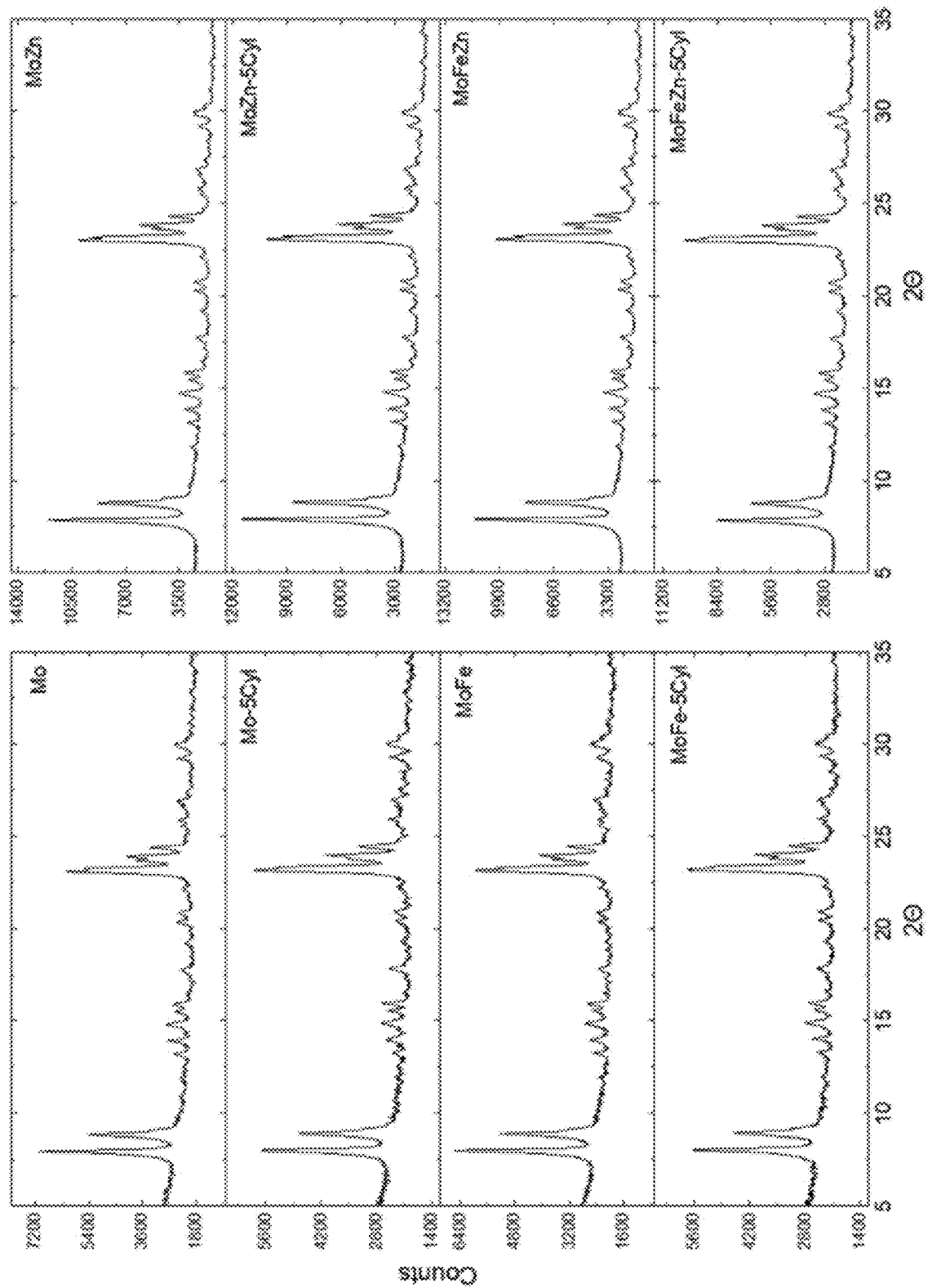
FIG. 8 shows representative X-ray diffraction (XRD) data obtained from representative disclosed catalysts as indicated in the figure. In the figure, the data were obtained from either the fresh indicated catalyst, e.g., "Mo" indicates that the data were obtained of a disclosed Mo catalyst, or after five cycles of use, e.g., "Mo-5Cyl" indicates a disclosed Mo catalyst after 5 cycles of use.

Catalyst Evaluation Methods: As shown in FIG. 8, the XRD patterns of the freshly prepared catalysts were compared to the regenerated catalyst. Considering the diffraction angles of 22-25°, the data show almost no changes were observed in the fresh catalyst diffraction pattern compared to the regenerated catalyst. Without wishing to be bound by a particular theory, it is believed that the data show that the ZSM-5 structure retained its crystallinity throughout the reaction and regeneration cycles. Furthermore, metal oxide peaks corresponding to Mo, Fe, or Zn could not be observed, indicating that the metal loadings were homogeneously dispersed and their particle sizes were small below the XRD detection limits (Lu, Y.; Wang, D.; Song, Y.; Yang, Q.; Fu, M.; Yu, D.; Fang, Y. Synthesis of hierarchical-structured Zn/Mo-HZSM-5 and its application in dimethy ether aromatization. Proceedings of the 2015 Asia-Pacific Energy Equipment Engineering Research Conference; Zhuhai, China, Jun. 13-14, 2015).

Figure 9:
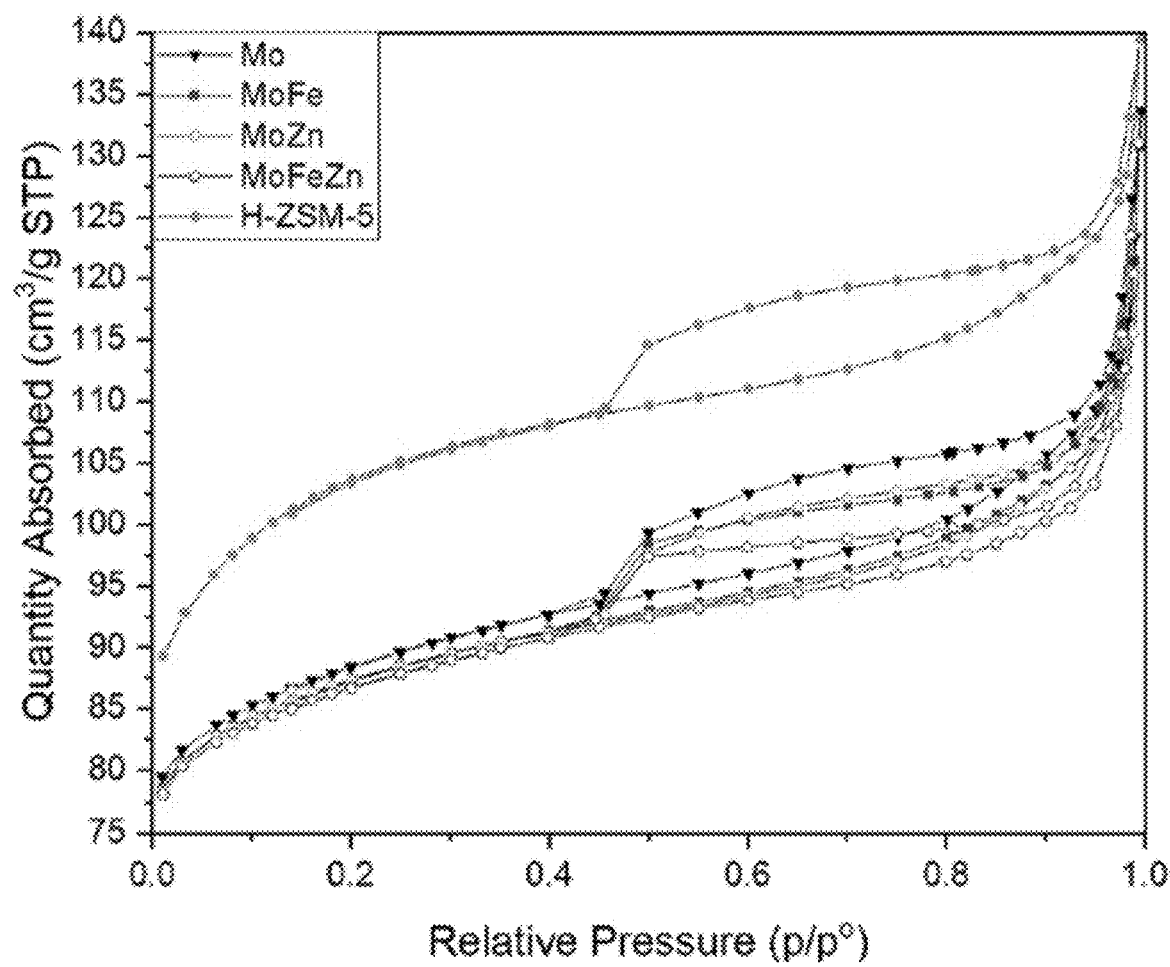
FIG. 9 shows representative nitrogen absorption-desorption isotherm data for the indicated disclosed catalyst or control (H-ZSM-5) comprising only zeolite. The data were obtained from fresh catalysts.

The nitrogen adsorption and desorption data are shown in FIG. 9 for fresh catalysts. The plot of H-ZSM-5 and all four metal-loaded ZSM-5 catalysts represent a type II isotherm. The large hysteresis loop observed in the range of PIP°=0.40-1.0 suggests that the catalyst have a mesoporous structure, where nitrogen condenses on the external surfaces of the crystallites and on the spaces in between. A summary of the surface area and micropore analysis is shown in Table 5.

TABLE 5

|  | Total Surface Area $(m^2/g)^a$ | Micropore Area $(m^2/g)^b$ | External Area $(m^2/g)^b$ | Pore Volume $(cm^3/g)$ |
|---|---|---|---|---|
| H-ZSM5 | 352 | 250 | 102 | 0.12 |
| Mo | 298 | 228 | 70 | 0.11 |
| MoFe | 294 | 228 | 66 | 0.11 |
| MoZn | 295 | 228 | 67 | 0.11 |
| MoFeZn | 292 | 227 | 66 | 0.11 |

$^a$Calculated using the BET method;
$^b$Calculated using the t-plot method.

The data in Table 4 show that addition of Mo to the unprompted zeolite resulted in a decrease in the total surface area, including the micropore area and the external surface area of the catalyst. As the total weight percent of the loaded metals increased, the total surface area of catalysts decreased. The addition of Fe to Mo/ZSM-5 resulted in a further decrease in the external surface area. However, the micropore area did not change compared to Mo/ZSM-5, suggesting that the Fe metal particles may not have diffused into the micropore structure of the zeolite. The addition of Zn to the Mo/ZSM-5 catalyst showed similar effects compared to Fe on the micropore area and external surface area. These data suggest that Zn can occupy external acid sites on the ZSM-5 structure with little to no diffusion into the pores of the ZSM-5 structure. For the MoFeZn/ZSM-5 catalyst, there was a total decrease in both the micropore area and external surface area compared to pure H-ZSM-5.

FIGS. 17A-17E show NH3-TPD profile data of H-ZSM-5 (control) and all four fresh catalysts. As shown in the figure, pure HZSM-5 exhibits two NH3 desorption peaks at 223 and 427° C., representing weak acid sites (mostly Lewis acid) and strong acid sites (mostly Brønsted acid), respectively. The presence of Mo particles anchored to the Brønsted acid sites on the external surface and inside the pores is evident from the decrease of the higher temperature peak shown in FIGS. 17A-17E and confirmed by the BET analysis discussed above for Table 4 (Liu, H.; Shen, W.; Bao, X.; Xu, Y. Appl. Catal., A 2005, 295 (1), 79-88). The addition of Fe and Zn to Mo/ZSM-5 did not cause a further decrease in the Brønsted acid strength. On the basis of the temperature shift and changes in peak shape, the addition of Mo, Fe, and Zn appear to have less impact on Lewis acid sites compared to Brønsted acid sites.

Figure 10A:
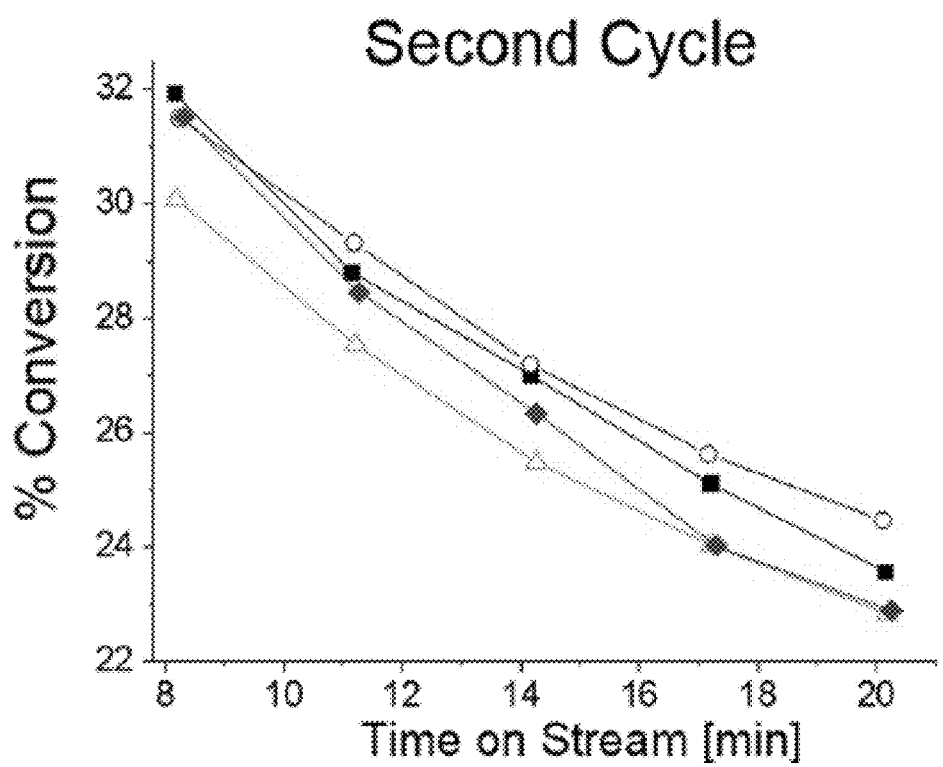
FIGS. 10A-10C show representative data for ethane conversion and average aromatic selective for the indicated catalyst.
Figure 10B:
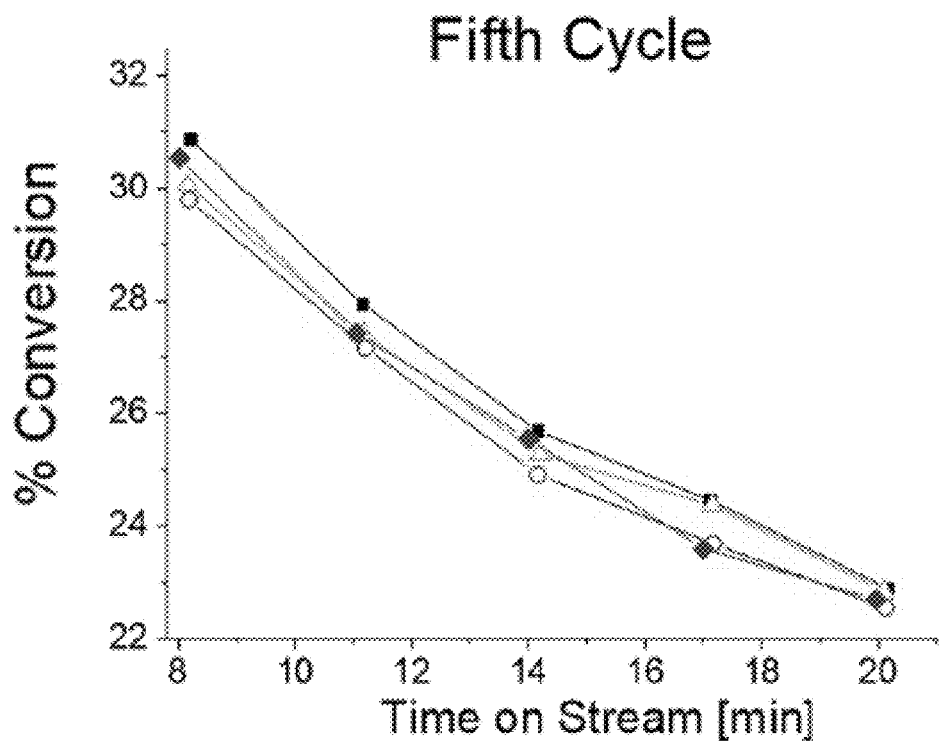
Figure 10C:
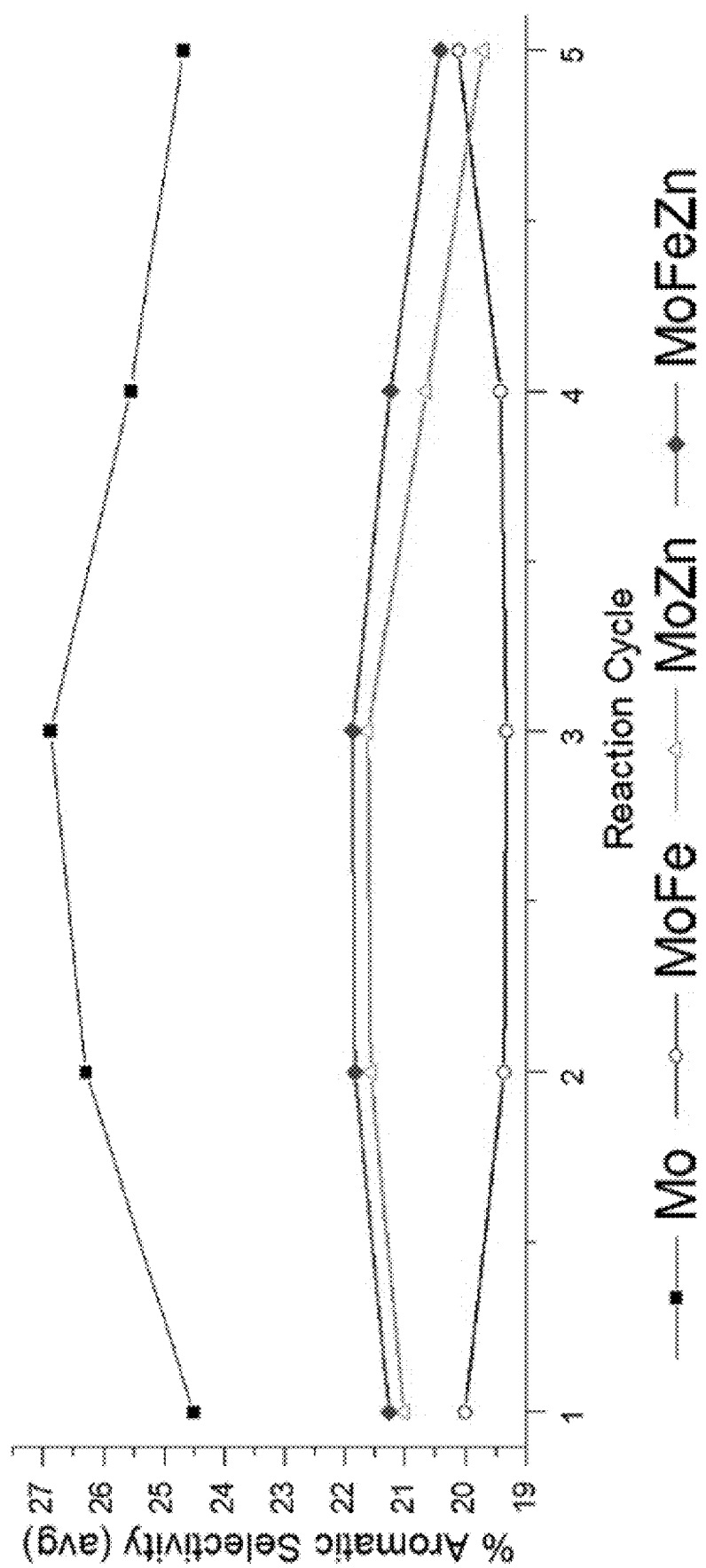
Figure 12A:
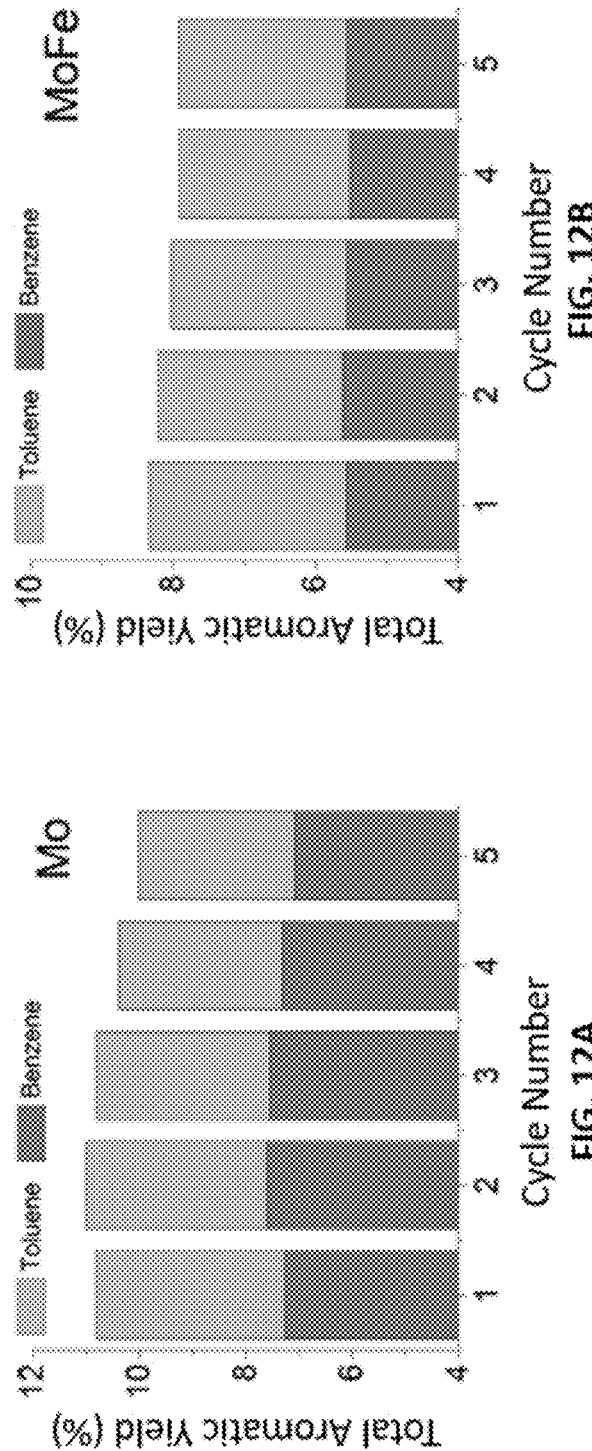
FIGS. 12A-12D show representative data obtained using disclosed catalysts for total aromatic yields (toluene and benzene, as indicated) for each of five reaction cycles as indicated.
Figure 12B:
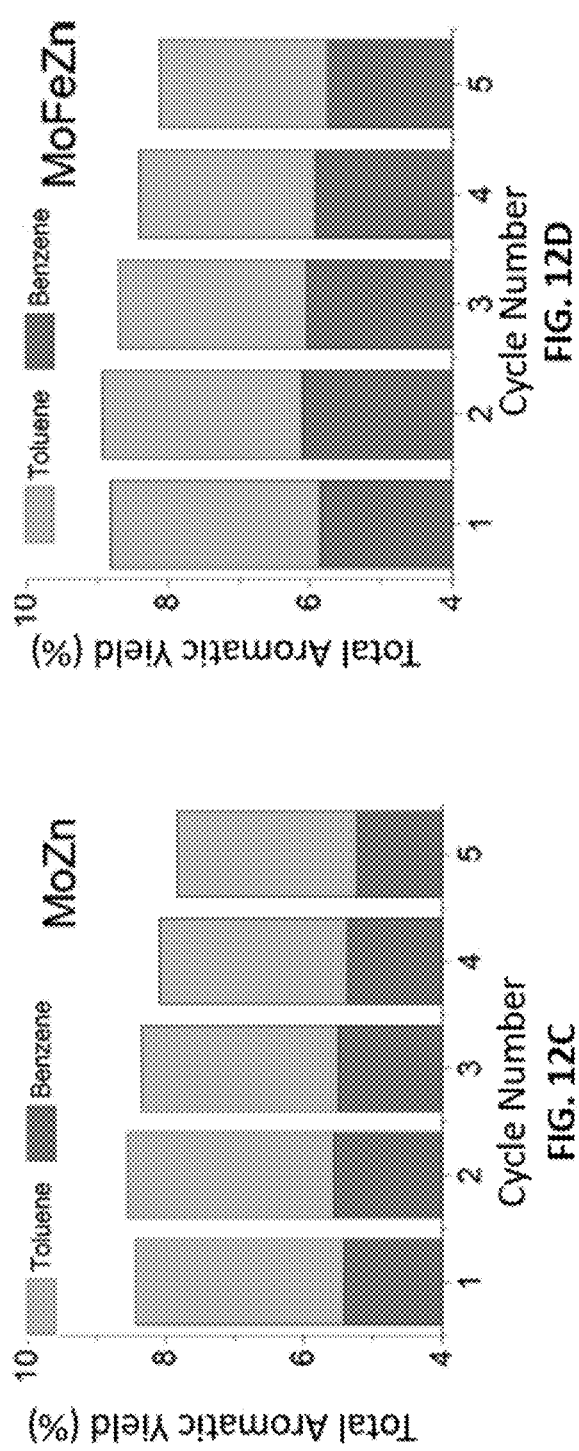
Figure 12C:
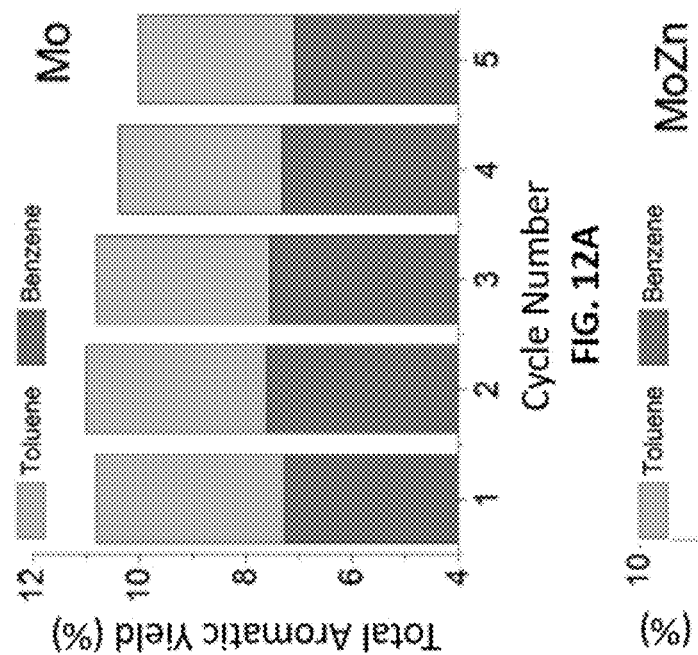
Figure 12D:
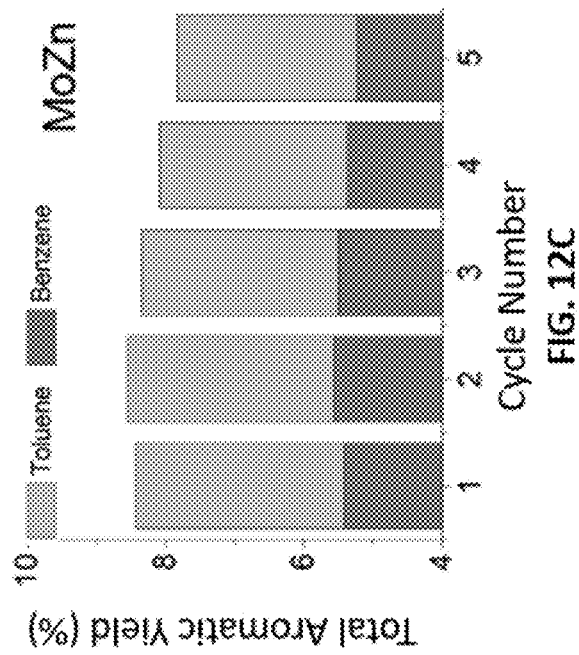
Figure 17A:
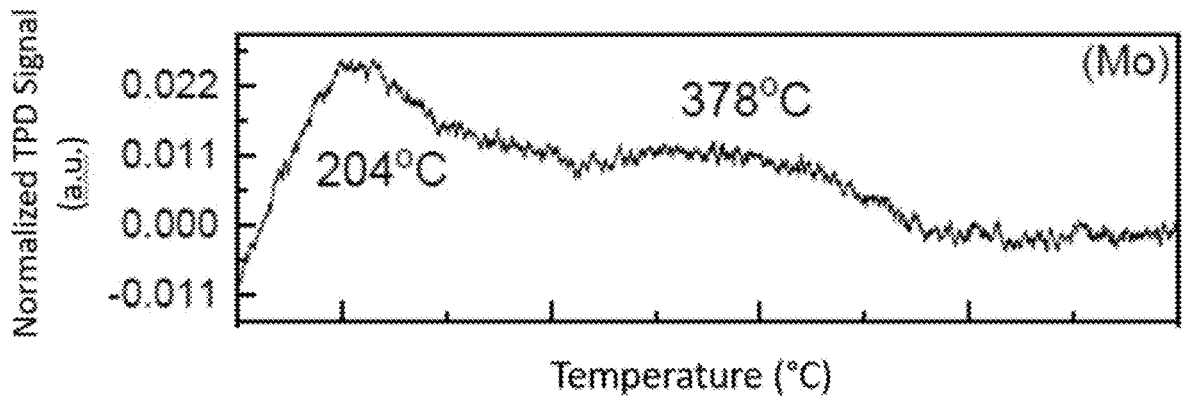
FIGS. 17A-17E show representative temperature-programmed desorption (TPD) profile data obtained using representative disclosed catalysts as indicated.
Figure 17B:
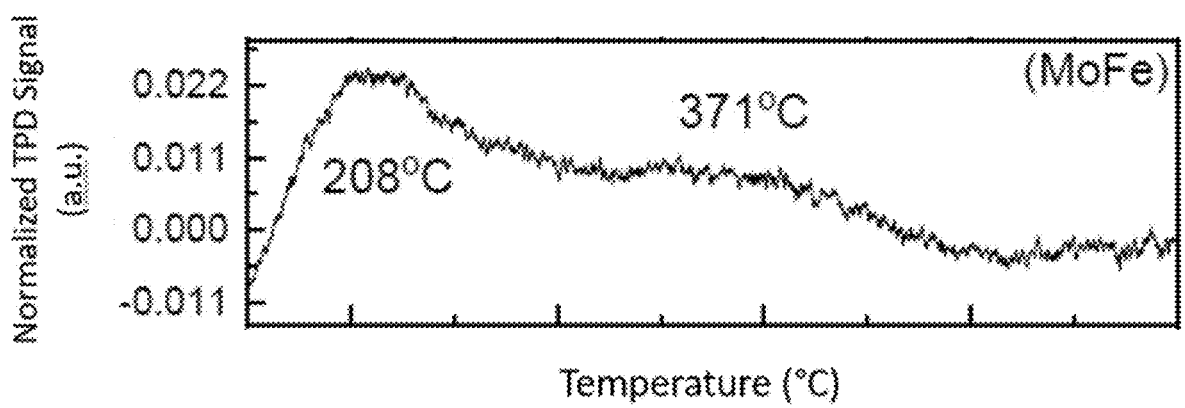
Figure 17C:
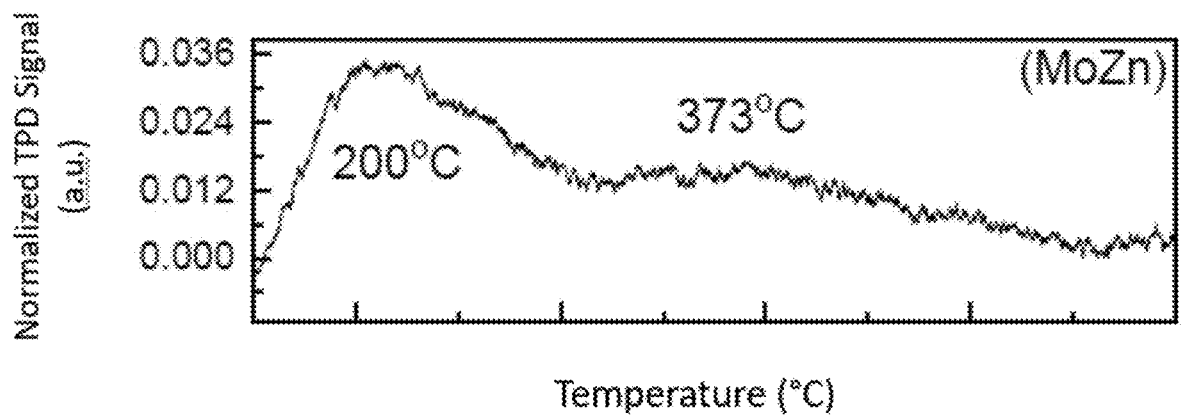
Figure 17D:
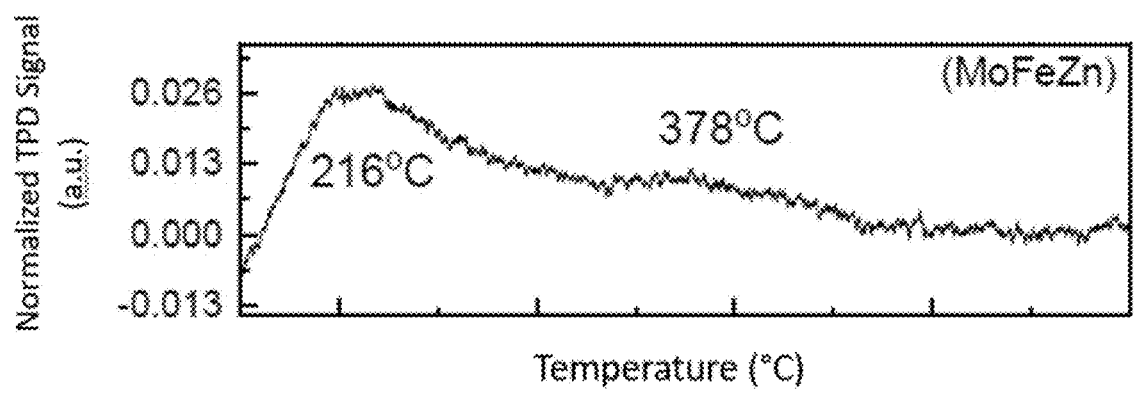
Figure 17E:
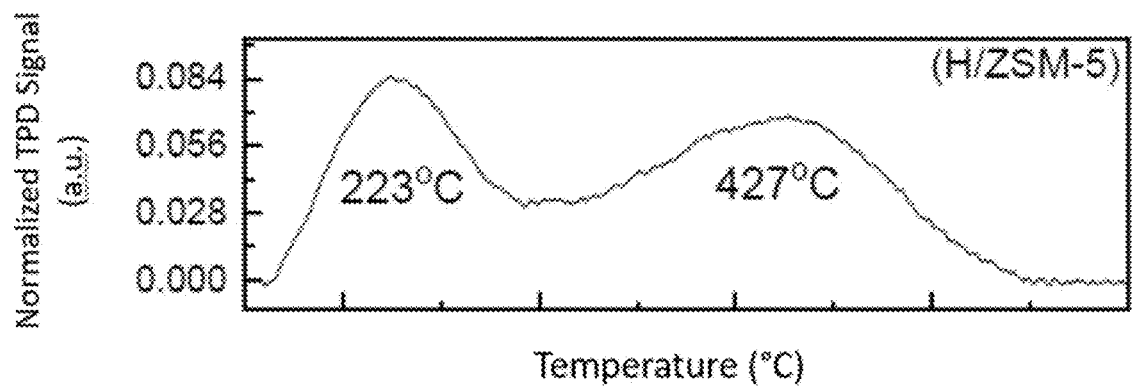

Catalyst Performance in Ethane Dehydroaromatization: FIGS. 10A-10C depicts the conversion and selectivity of each catalyst toward ethane dehydroaromatization. The second cycle was chosen as a basis for comparison throughout Example 2, in part to the presence of the induction period in the fresh catalyst which increased the difficultly to compare the activity in the first cycle. The promoting effect of metals on ZSM-5 was ranked on the basis of ethane conversion. The ethane conversion level for the second cycle (FIG. 10A) was found in the order of MoFe>Mo>MoFeZn>MoZn, whereas for the fifth cycle (FIG. 10B), the conversion level followed the order of Mo>MoZn≈MoFeZn>MoFe. The aromatic selectivity of these catalysts with respect to regeneration cycles is shown in FIG. 10C. Although the selectivity of the MoFe catalyst to aromatics was relatively lower than others, it showed stable aromatic selectivity with little to no decrease in the average selectivity from the second to fourth reaction cycle and even a slight increase on the fifth cycle. The MoZn catalyst showed a slight increase in the overall average aromatic selectivity from the first to third reaction cycle. However, a decrease was observed from the third to fifth reaction cycle. The MoFeZn catalyst exhibited a trend similar to the MoZn catalyst; however, the slope of the deactivation of aromatic selectivity was less severe from the third to fifth cycle.

Without wishing to be bound by a particular theory, it is believed these data suggest that Fe had a stabilizing effect on the MoFeZn catalyst as it did in the MoFe catalyst. It is possible that the presence of Zn can promote selectivity to aromatics in ethane aromatization as a result of the type of Zn sites formed (Liu, H.; Shen, W.; Bao, X.; Xu, Y. Appl. Catal., A 2005, 295 (1), 79-88). Without wishing to be bound by a particular theory, the increase in selectivity to aromatics on MoZn and MoFeZn catalysts over the first to third cycles could be due to the formation of zinc hydroxyl species. However, after the third reaction cycle, a decline in aromatic selectivity was observed. Without wishing to be bound by a particular theory, it is possible that this decline may be associated with a loss of the Zn species (Lai, Y.; Veser, G. Environ. Prog. Sustainable Energy 2016, 35 (2), 334-344). Table 4 showed the ICP analysis of spent catalysts after five reaction/regeneration cycles; the Zn content decreased by nearly 50%. Without wishing to be bound by a particular theory, it is possible that this could be due to loss of volatile unbound ZnO species, thus leaving the more stable and active $[Zn(OH)]^+$ species bound to the acid sites of the zeolite surface (Abdelsayed, V.; Smith, M. W.; Shekhawat, D. Appl. Catal., A 2015, 505, 365-374).

FIGS. 11A-11D show the benzene concentration as a function of time-on-stream (TOS) for the catalysts described in this Example. Overall, the data show that the Mo/ZSM-5 catalyst was associated with the highest benzene concentration, followed by MoFe, MoFeZn, and MoZn catalysts. To study the commercial viability of cyclic regeneration, for each catalyst, the extent of deactivation between each regeneration cycle was analyzed. In some respects, a stable catalyst should exhibit the characteristics that the time-on-stream benzene concentration in all five cycles falls on the same line. Such a behavior would be indicative of a catalyst that is regenerable and can be used repeatedly. In contrast, if a divergence of the benzene concentration between cycles is observed, that would be suggestive of either irreversible deactivation or an inefficient regeneration process. Understanding the cause of the "divergence" between cycles can be important in developing a commercially viable catalyst and regeneration process. The numerical data in FIGS. 11A-11D are quantitatively broken down to give the percent change in the benzene concentration from cycle to cycle for each catalyst and then an overall change from the second to fifth reaction cycle. Date are summarized in Table 6 below showing that the MoFe catalyst exhibits little to no decrease in the benzene concentration from cycle to cycle. The other three catalysts show some loss of activity and irreversibility between cycles.

TABLE 6

| Time | Benzene Concentration Change Per Cycle | | | | |
|---|---|---|---|---|---|
| [Min] | 1-->2 | 2-->3 | 3-->4 | 4-->5 | 2-->5 |
| Mo | | | | | |
| 8 | −390 | 77 | 81 | 198 | 355 |
| 12 | −259 | 46 | 188 | 150 | 384 |
| 16 | −211 | 41 | 173 | 178 | 393 |
| 20 | −143 | −11 | 243 | 131 | 363 |
| MoFe | | | | | |
| 8 | −19 | 20 | 76 | −91 | 5 |
| 12 | −48 | 80 | 6 | −22 | 65 |
| 16 | −32 | 46 | 12 | −23 | 35 |
| 20 | 5 | −10 | 72 | −10 | 52 |
| MoZn | | | | | |
| 8 | −78 | 2 | 142 | 83 | 227 |
| 12 | −94 | 29 | 89 | 115 | 233 |
| 16 | −150 | 70 | 79 | 112 | 261 |
| 20 | −138 | 91 | 109 | 96 | 296 |
| MoFeZn | | | | | |
| 8 | −187 | 46 | 86 | 148 | 280 |
| 12 | −194 | 70 | 89 | 108 | 267 |
| 16 | −159 | 24 | 133 | 104 | 262 |
| 20 | −197 | 57 | 62 | 142 | 262 |

Similarly, MoFe exhibits the same behavior toward the toluene formation during these 5 reaction cycles (see FIGS. 18A-18D; and Table 7 below). The variation in the toluene concentration was fairly minimal among other catalysts studied during these five reaction cycles. The variation that was seen, without wishing to be bound by a particular theory, could be attributed to the buildup of coke on the interior surface of the pores and thereby resulting in a decrease in the diameter of the pore. Furthermore, a decrease in the pore diameter could lead to the toluene disproportionation reaction to form benzene and xylene (Fang, L.-Y.; Liu, S.-B.; Wang, I. J. Catal. 1999, 185 (1), 33-42). Without wishing to be bound by a particular theory, this may also be an explanation that, for the MoFe catalyst, little to no decrease in the benzene concentration was observed between cycles, whereas a slight decrease in the toluene concentration continued.

TABLE 7

| Time | Toluene Concentration Change Per Cycle | | | | |
|---|---|---|---|---|---|
| [Min] | 1-->2 | 2-->3 | 3-->4 | 4-->5 | 2-->5 |
| Mo | | | | | |
| 8 | 100 | 158 | 112 | 143 | 413 |
| 12 | 108 | 118 | 145 | 107 | 370 |
| 16 | 89 | 96 | 126 | 119 | 341 |
| 20 | 83 | 68 | 152 | 94 | 313 |
| MoFe | | | | | |
| 8 | 146 | 111 | 101 | −13 | 200 |
| 12 | 124 | 117 | 44 | 24 | 184 |
| 16 | 116 | 91 | 40 | 15 | 147 |
| 20 | 118 | 56 | 60 | 22 | 138 |
| MoZn | | | | | |
| 8 | 82 | 91 | 124 | 85 | 300 |
| 12 | 50 | 89 | 100 | 83 | 272 |
| 16 | 7 | 96 | 81 | 87 | 263 |
| 20 | −13 | 106 | 100 | 82 | 288 |
| MoFeZn | | | | | |
| 8 | 152 | 141 | 130 | 106 | 378 |
| 12 | 126 | 141 | 106 | 86 | 333 |
| 16 | 96 | 116 | 118 | 83 | 318 |
| 20 | 57 | 107 | 86 | 102 | 294 |

FIGS. 12A-12D show data for the distribution of total aromatic yields of the four catalysts assessed in Example 2. The total aromatic (benzene and toluene) yield followed the order of Mo>MoFeZn>MoFe>MoZn supported on ZSM-5. For each of these catalysts, starting from the second cycle, a trend of decrease in the total aromatic yield was observed on Mo, MoZn, and MoFeZn catalysts. However, the MoFe catalyst shows no decrease in the benzene yield but a slight decrease in the total aromatic yield as a result of the toluene disproportionation reaction.

FIGS. 19A-19D show data for a comparison of the hydrogen production rates between the four catalysts of Example 2. The initial activity of hydrogen production rates was in the following order: MoFeZn>Mo≈MoFe>MoZn, where Mo and MoFe catalysts exhibited comparable hydrogen production rates and the MoZn catalyst was the lowest. MoFeZn showed the highest initial production rate, and without wishing to be bound by a particular theory, this could be attributable to a higher metal loading. The MoFe catalyst showed the least amount of reduction in the hydrogen concentration per cycle as shown in Table 8 below. The data in Table 8 are consistent with the time-on-stream changes of benzene and toluene concentrations, as shown in FIGS. 11A-11D and 18A-18D.

TABLE 8

| Time | Hydrogen Change Per Cycle | | | | |
|---|---|---|---|---|---|
| [Min] | 1-->2 | 2-->3 | 3-->4 | 4-->5 | 2-->5 |
| Mo | | | | | |
| 8 | −0.13 | 0.25 | 0.19 | 0.21 | 0.65 |
| 12 | −0.01 | 0.19 | 0.70 | 0.27 | 0.66 |
| 16 | 0.01 | 0.19 | 0.22 | 0.20 | 0.62 |
| 20 | 0.03 | 0.17 | 0.22 | 0.19 | 0.58 |
| MoFe | | | | | |
| 8 | −0.23 | 0.20 | 0.26 | −0.01 | 0.44 |
| 12 | −0.13 | 0.12 | 0.19 | −0.01 | 0.30 |
| 16 | −0.15 | 0.14 | 0.10 | 0.00 | 0.24 |
| 20 | −0.11 | 0.05 | 0.06 | 0.04 | 0.15 |
| MoZn | | | | | |
| 8 | −0.24 | 0.14 | 0.19 | 0.18 | 0.50 |
| 12 | −0.28 | 0.17 | 0.18 | 0.18 | 0.53 |
| 16 | −0.21 | 0.15 | 0.23 | 0.14 | 0.52 |
| 20 | −0.16 | 0.13 | 0.20 | 0.15 | 0.47 |
| MoFeZn | | | | | |
| 8 | −0.03 | 0.20 | 0.29 | 0.36 | 0.85 |
| 12 | 0.02 | 0.19 | 0.25 | 0.30 | 0.75 |
| 16 | 0.01 | 0.22 | 0.21 | 0.24 | 0.67 |
| 20 | 0.02 | 0.23 | 0.18 | 0.20 | 0.62 |

FIGS. 20A-20A of the Supporting Information depicts the time-on-steam methane formation rate for all catalysts studied. The activity of methane formation is in the order of MoFeZn>Mo≈MoFe>MoZn supported on ZSM-5. The changes in the methane concentration between cycles are summarized in Table 9 below. The data show that from the second to fifth cycle, Mo and MoFeZn exhibited comparable changes in the methane formation rate, whereas the MoFe catalyst resulted in little to no change in the methane concentration. The data are consistent with the data regarding concentration changes for benzene, toluene, and hydrogen shown in FIGS. 11A-11D, 18A-18D, and 19A-19D.

TABLE 9

| Time | Change in Methane Per Cycle | | | | |
|---|---|---|---|---|---|
| [Min] | 1-->2 | 2-->3 | 3-->4 | 4-->5 | 5-->6 |
| Mo | | | | | |
| 8 | −0.16 | −0.02 | 0.03 | 0.04 | 0.05 |
| 12 | −0.06 | 0.00 | 0.02 | 0.06 | 0.08 |
| 16 | −0.06 | 0.01 | 0.05 | 0.03 | 0.09 |
| 20 | −0.05 | 0.00 | 0.04 | 0.03 | 0.07 |
| MoFe | | | | | |
| 8 | −0.13 | 0.02 | 0.03 | −0.03 | 0.02 |
| 12 | −0.08 | −0.01 | 0.02 | −0.02 | −0.01 |
| 16 | −0.06 | 0.00 | −0.01 | 0.00 | −0.01 |
| 20 | −0.05 | 0.00 | −0.01 | −0.01 | −0.02 |
| MoZn | | | | | |
| 8 | −0.15 | −0.02 | 0.01 | 0.07 | 0.06 |
| 12 | −0.12 | 0.00 | 0.01 | 0.02 | 0.03 |
| 16 | −0.09 | −0.01 | 0.02 | 0.01 | 0.03 |
| 20 | −0.07 | 0.00 | 0.01 | 0.02 | 0.02 |
| MoFeZn | | | | | |
| 8 | −0.18 | 0.01 | 0.03 | 0.09 | 0.13 |
| 12 | −0.13 | 0.01 | 0.03 | 0.05 | 0.08 |
| 16 | −0.10 | 0.01 | 0.02 | 0.03 | 0.07 |
| 20 | −0.08 | 0.02 | 0.02 | 0.02 | 0.06 |

Mechanistic Study of Catalyst Deactivation and Regeneration: To assess the catalyst deactivation mechanism and the effectiveness of regeneration, TEM/EDS analysis was carried out. TEM images of the four catalysts assessed in Example are shown in FIGS. 13A-13C, 14A-14C, and 15A-15C. FIG. 13A shows TEM of a spent Mo catalyst after five reaction cycles.

Agglomeration of Mo particles was observed, as confirmed using EDS analysis (spot 1, FIG. 13A). A spent MoFe catalyst is shown in FIG. 13B along with the EDS analysis for spots 1 and 2. The formation of CNTs was observed. Spot 1 (FIG. 13A) contained a high concentration of carbon along with agglomerated metal particles that have a Fe/Mo atomic ratio of 12.65 (see FIG. 13C for the EDS analysis of the indicated spots in images in FIGS. 13A and 13B). Spot 1 (FIG. 13A) did not show any support structure (Si and Al), indicating that the metal agglomerates may have leached out the surface of the catalyst during the reaction. Spot 2 (FIG. 13B) also contained a large amount of carbon; however, the agglomerated particle shows a Fe/Mo ratio of 1.2 and was located on the surface of the zeolite. This would suggest, without wishing to be bound by a particular theory, that at a larger Fe/Mo ratio, the agglomerated MoFe particles may tend to leave the surface of the catalyst. In addition, both tip-growth and base-grown CNTs can be observed in TEM analysis.

TEM images of the spent MoZn catalyst are shown in FIGS. 14A and 14B, and EDS analysis of these images is shown in FIG. 14C. Spot 1 (FIG. 14A) contained a large atomic percentage of Mo and Zn, with a Zn/Mo atomic ratio of 1.78 (see FIG. 14C for EDS analysis of the indicated spots in images in FIGS. 14A and 14B), located on a support structure with some carbon deposited. On spot 2 (FIG. 14A), the presence Mo and Zn was not observed, suggesting that the metal particles were not located in this area or that the density of metal particles was too small as a result of even dispersion. Spot 3 (FIG. 14B) contained a high concentration of Mo and Zn, with a Zn/Mo atomic ratio of 0.97. On spot 4, Zn or Mo was not found, suggesting the uniform dispersion in that area or the migration of metals to the spot 3 area.

TEM images of the spent MoFeZn catalyst are shown in FIGS. 15A and 15B, and EDS analysis of these images is shown in FIG. 15C. On spot 1, the TEM image showed agglomerated Mo and Fe particles that were not located on the zeolite support. On spot 1 (FIG. 15A), the Fe/Mo atomic ratio is 1.63 (see FIG. 15C for EDS analysis of the indicated spots in images in FIGS. 15A and 15B). This is representative of tip-growth CNT, where the Mo—Fe agglomerates pushed out to leave the surface of the zeolite support. Spot 2 (FIG. 15B) contained agglomerated Fe and Mo, with a much lower Fe/Mo ratio of 0.47. Spot 3 (FIG. 15B) was another spot where a lower Fe/Mo ratio of 0.40 was observed. Without wishing to be bound by a particular theory, it is possible that the lower atomic ratios could be explained, in part, by Masiero et al. (Masiero, S. S.; Marcilio, N. R.; Perez-Lopez, O. W. Catal. Lett. 2009, 131 (1-2), 194-202), in which it was observed that Fe interacted structurally with Mo to form a new binary phase of $Fe_2(MoO_4)_3$. An atomic ratio of Fe and Mo in $Fe_2(MoO_4)_3$ can be calculated to be about 0.41. The Fe/Mo ratio in $Fe_2(MoO_4)_3$ calculated was found in the EDS analysis on spots 2 and 3 (FIG. 15B). Without wishing to be bound by a particular theory, it may be possible that $Fe_2(MoO_4)_3$ was formed on the MoFeZn catalyst. The data suggests that at lower Fe/Mo ratios, the Fe and Mo agglomerates may stay attached to the zeolite support structure, whereas at higher Fe/Mo ratios, excess amounts of Fe allow for agglomerated particles to detach from the surface.

ICP results shown in Table 4 suggest a small loss in Fe particles in the spent catalysts containing Fe, which is consistent with most Fe particles are deposited back onto the surface of the catalyst during regeneration. However, some Fe particles, without wishing to be bound by a particular theory, may be deposited onto the reactor walls. ICP analysis also suggests that the MoFeZn catalyst lost less Mo than the MoZn catalyst, without wishing to be bound by a particular theory, may indicate that Fe is a more stable promoter for Mo than Zn. The loss of Zn and Fe particles from the catalyst surface may follow different mechanisms. Without wishing to be bound by a particular theory, it is possible that the loss of Zn is due to the presence of the volatile state of zinc oxide (Abdelsayed, V.; Smith, M. W.; Shekhawat, D. Appl. Catal., A 2015, 505, 365-374). In contrast, without wishing to be bound by a particular theory, it is possible that the loss of Fe occurs in a more random way, possibly due to the formation of tip-growth CNTs extending randomly away from the catalyst surface.

Catalyst Characterization using TPO and TPA Methods: TPO analysis was used to qualitatively to characterize types of coke formed on the catalyst surfaces during reaction based on the peak shape and burn-off temperatures. The peak shape of Mo and MoZn catalysts was suggestive of the presence of a single temperature burning carbonaceous species with resulting peak temperatures of 445° C. Twin-peak TPO spectra were observed on MoFe and MoFeZn catalysts. A second peak was associated with the presence of higher burning temperature carbon species (516° C.). TPO analysis suggested that the addition of Fe results in the formation of a higher ordered coke species, e.g., CNTs, as observed from TEM analysis.

The TGA profile of the spent Mo and MoZn catalysts resulted in one continuous negative curvature, whereas for MoFe and MoFeZn catalysts, the TGA curvature has a positive rise in slope at the temperature of the lowest point between the two peaks in the TPO profiles. The TGA results for all four catalysts are summarized below in Table 10. As shown therein, MoFe and MoFeZn catalysts were more selective toward coke formation, which is consistent with literature reports (Burns, S.; Hargreaves, J. S. J.; Pal, P.; Parida, K. M.; Parija, S. Catal. Today 2006, 114 (4), 383-387; Masiero, S. S.; Marcilio, N. R.; Perez-Lopez, O. W. Catal. Lett. 2009, 131 (1-2), 194-202; and Liu, S.; Dong, Q.; Ohnishi, R.; Ichikawa, M. Chem. Commun. 1997, 1455-1456). The Mo catalyst showed the highest conversion with 25% less coke than the MoFe catalyst.

TABLE 10

| Catalyst | Total Coke (mg) | Carbon Formation (g g$^{-1}$ of catalyst min$^{-1}$) |
| --- | --- | --- |
| Mo | 2.49 | 0.118 |
| MoFe | 3.10 | 0.147 |
| MoZn | 2.38 | 0.113 |
| MoFeZn | 3.08 | 0.146 |

Catalyst Characterization using TPR Methods: FIGS. 16A-16D show TPR profiles for the fresh and regenerated catalysts (fifth cycle). For both Mo and MoZn catalysts, a temperature shift of 51° C. (first peak from 473 to 422° C.) was observed between fresh and spent catalysts. However, for the catalysts containing Fe, only a 27° C. shift in the temperature of the first peak was, suggestive of a more stable metal state. For the spent catalyst obtained after five cycles, the peak shape of MoFe was identical to MoFeZn, whereas the peak shape of Mo was almost identical to MoZn.

Without wishing to be bound by a particular theory, it is possible that is attributed to the loss of Zn over the course of the five cycles, as shown in the ICP analysis (discussed herein above); therefore, the impact of Zn on stabilizing Mo may gradually diminish as the number of reaction cycles increases.

As shown herein, the data for Example 2 show the stability of Fe- and Zn-promoted Mo in ethane dehydroaromatization over five cycles of reaction and regeneration. All catalysts in Example 2 were found to maintain their zeolite crystalline structure. Mo was determined to be in the pores and on the exterior surface with strong interactions with Brønsted acid sites. On Fe- and Zn-promoted Mo catalysts, Fe and Zn were located mainly on the exterior surface. The Mo-containing ZSM-5 catalyst exhibited the highest conversion and aromatic yield with some loss in activity between reaction cycles. The addition of Zn resulted in an increase in aromatic selectivity during early reaction cycles but suffered a decrease in selectivity in the consecutive reaction cycles. The promoting effect of Zn in cyclic operation was associated with a loss of almost 50% Zn over the course of the 5 reaction cycles. The initial increase in selectivity may be atttributable to the formation of zinc hydroxide species, $[Zn(OH)]^+$.

The addition of Fe resulted in great stability in aromatic selectivity, total aromatic yield, and hydrogen formation rate over the course of five reaction cycles. The improved stability was attributed to the formation of CNTs that allowed for improved gas diffusion into the pores. At lower Fe/Mo atomic ratios, the agglomerated particles were found on the surface of the catalyst, resulting in the favored base growth CNTs. At higher Fe/Mo ratios, tip-growth CNTs were observed, which, without wishing to be bound by a particular theory, is believed to associated with a loss of Fe and Mo. MoZn lost more Mo than MoFeZn, suggesting that Mo may be more stable in the presence of Fe than it was with Zn. Metal particles with a lower Fe/Mo atomic ratio may result in even greater stability.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method for conversion of natural gas to higher hydrocarbons, the process comprising:
   arranging a catalyst in a reaction chamber of a reactor;
      wherein the catalyst comprises a zeolite present in an amount of about 80 wt % to about 99.95 wt % based on the total weight of the catalyst;
      wherein the catalyst comprises a first metal or metal oxide and a second metal or metal oxide;
      wherein the first metal or metal oxide is present in an amount of about 0.05 wt % to about 20 wt %; and
      wherein the second metal or metal oxide is present in an amount of about 0.05 wt % to about 20 wt %, provided that the second metal or metal oxide is not the same as the first metal or metal oxide;
   conveying a flow of a first inert gas, a reducing gas, or a combination of the first inert gas and the reducing gas into the reaction chamber and contacting the catalyst;
   pre-heating the catalyst in the reaction chamber using microwave energy;

conveying a flow of a feedstock gas into the reaction chamber and contacting the catalyst;

reacting the feedstock gas on the catalyst, thereby converting at least a portion of the feedstock gas to higher hydrocarbons;

wherein the reactor comprises a microwave energy apparatus configured to provide microwave energy to the reaction chamber of the reactor;

wherein the reaction chamber is configured to allow a continuous flow of a feedstock gas to the reaction chamber; and wherein the feedstock gas comprises natural gas comprising C1-C6 alkanes.

2. The method of claim 1, wherein the first metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof; and wherein the second metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof, provided that the second metal oxide is not the same as the first metal oxide.

3. The method of claim 2, wherein the first metal or metal oxide is selected from molybdenum, platinum, and gallium; and wherein the second metal or metal oxide is selected from iron, zinc, and platinum, provided that the second metal oxide is not the same as the first metal oxide.

4. The method of claim 1, further comprising a third metal or metal oxide, and wherein the third metal or metal oxide is present in an amount of about 0.05 wt % to about 10 wt %, provided that the third metal oxide is not the same as the first metal oxide or the second metal oxide.

5. The method of claim 4, wherein the first metal or metal oxide is present in an amount of about 0.05 wt % to about 5 wt %; wherein the second metal or metal oxide is present in an amount of about 0.1 wt % to about 5 wt %; and wherein the third metal or metal oxide is present in an amount of about 0.1 wt % to about 5 wt %.

6. The method of claim 4, wherein the third metal or metal oxide is selected from scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, aluminum, gallium, tin, and combinations thereof, provided that the third metal oxide is not the same as the first metal oxide or the second metal oxide.

7. The method of claim 6, wherein the third metal or metal oxide is selected from iron, zinc, molybdenum, platinum, and gallium.

8. The method of claim 1, wherein the reactor is a fixed-bed reactor; or wherein the reactor is a moving-bed reactor.

9. The method of claim 1, wherein the pre-heating the catalyst is carried out at a catalyst heating temperature of about 300° C. to about 1000° C.

10. The method of claim 1, wherein the first inert gas is helium, argon, nitrogen, or combinations thereof.

11. The method of claim 1, wherein the natural gas comprises about 70 vol % to about 100 vol % methane.

12. The method of claim 1, wherein the feedstock gas comprises greater than or equal to about 90 vol % natural gas.

13. The method of claim 12, wherein the feedstock gas comprises substantially only natural gas.

14. The method of claim 1, wherein the feedstock gas comprises about 5 vol % to about 100 vol % of the natural gas and about 0 vol % to about 90 vol % of a second inert gas.

15. The method of claim 14, wherein the second inert gas is helium, argon, nitrogen, or combinations thereof.

16. The method of claim 1, wherein about 5 vol % to about 90 vol % of the natural gas is converted to higher hydrocarbons.

17. The method of claim 1, wherein about 10 vol % to about 80 vol % of the natural gas is converted to the aromatic hydrocarbons comprising a mixture of benzene, toluene, xylene, and C9 or greater aromatic compounds.

18. The method of claim 1, wherein about 10 wt % to about 80 wt % of the higher hydrocarbons comprise C6 or higher hydrocarbons.

19. The method of claim 18, wherein about 30 wt % to about 70 wt % of the C6 or higher hydrocarbons comprise a mixture of benzene, toluene, and xylene.

20. The method of claim 1, wherein pre-heating the catalyst in the reaction chamber using microwave energy comprises irradiation with microwave energy having at a frequency of from about 1 MHz to about 50 GHz.

* * * * *